United States Patent [19]
Kobayashi et al.

[11] Patent Number: 5,574,033
[45] Date of Patent: *Nov. 12, 1996

[54] HETEROCYCLIC COMPOUND AND CARDIOTONIC AGENT CONTAINING THE SAME AS EFFECTIVE COMPONENT

[75] Inventors: Hideshi Kobayashi, Tokyo; Kimitomo Yoshioka, Kiyose; Hiroaki Yamazaki, Fujishiro-machi, all of Japan

[73] Assignee: Zenyaku Kogyo Kabushiki Kaisha, Tokyo, Japan

[*] Notice: The term of this patent shall not extend beyond the expiration date of Pat. No. 5,446,042.

[21] Appl. No.: 505,112

[22] Filed: Jul. 21, 1995

Related U.S. Application Data

[63] Continuation of Ser. No. 244,195, filed as PCT/JP92/01548, Nov. 27, 1992, Pat. No. 5,446,042.

[30] Foreign Application Priority Data

Nov. 29, 1991 [JP] Japan ................................. 3-340273

[51] Int. Cl.$^6$ .................. A61K 31/54; C07D 285/16; C07D 253/06; C07D 237/04
[52] U.S. Cl. .................. 514/222.5; 514/242; 514/252; 544/8; 544/182; 544/238; 544/239
[58] Field of Search ................. 514/222.5, 242, 514/252; 544/8, 182, 238, 239

[56] References Cited

U.S. PATENT DOCUMENTS

| | | | |
|---|---|---|---|
| 4,486,431 | 12/1984 | Lesher et al. | 544/238 |
| 4,788,194 | 11/1988 | Hargreaves et al. | 514/242 |
| 5,446,042 | 8/1995 | Kobayashi et al. | 514/222.5 |

*Primary Examiner*—Yogendra N. Gupta
*Attorney, Agent, or Firm*—Oblon, Spivak, McClelland, Maier & Neustadt, P.C.

[57] ABSTRACT

Heterocyclic compounds of the formula:

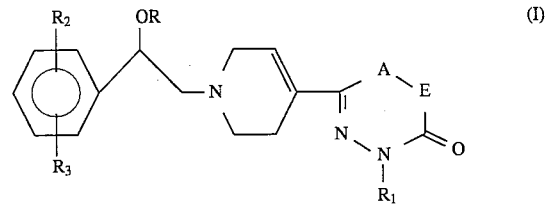

and a cardiotonic agent containing the same which have an excellent positive inotropic effect and which suppress increase of heart rate.

15 Claims, No Drawings

1

HETEROCYCLIC COMPOUND AND CARDIOTONIC AGENT CONTAINING THE SAME AS EFFECTIVE COMPONENT

This is a Continuation, of application Ser. No. 08/244,195 filed on May 27, 1994, now U.S. Pat No. 5,446,042 allowed, which was filed as International Application No. PCT/JP92/01548 on Nov. 27, 1992.

TECHNICAL FIELD

The present invention relates to heterocyclic compounds represented by the formula (I) or pharmaceutically acceptable acid addition salts thereof and cardiotonic agents containing the heterocyclic compounds as effective components:

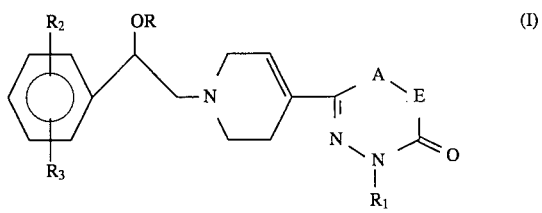

wherein

R and $R_1$ represent hydrogen atom or lower alkyl group;

$R_2$ and $R_3$ may be independently same or different and represent hydrogen atom, lower alkyl group, lower alkoxy group, trifluoromethyl group. halogen atom, nitro group, amino group, cyano group or hydroxyl group or $R_2$ and $R_3$ are joined to form methylenedioxy group or

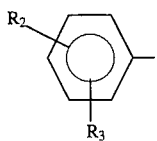

forms naphthalene; and A–E represents

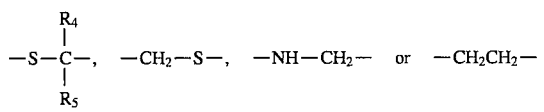

wherein $R_4$ and $R_5$ represent hydrogen atom or lower alkyl group.

BACKGROUND ART

Compounds represented by the following formula (II) are known as heterocyclic compounds having cardiotonic activity and are disclosed for example in Japanese Patent Provisional Publication (Kokai) Nos. 57-2284 and 58-131981 and Japanese Patent Publication (Kokoku) No. 61-53350.

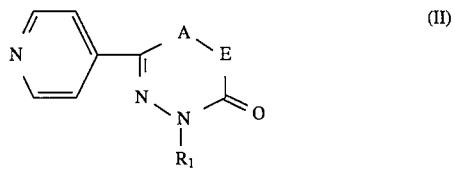

wherein $R_1$ and A–E are as defined above.

These known heterocyclic compounds having cardiotonic activities were clinically unfavorable since they have not so strong cardiotonic activities and increase heart rate.

We, the inventors carried out studies to succeed in synthesizing novel heterocyclic compounds having excellent positive inotropic effect as cardiotonic agent and suppressing increase of heart rate, by modifying the pyridyl group in the compound of the formula (II), thus completing the present invention. More specifically, the present invention is directed to tetrahydropyridine derivatives represented by the above-mentioned formula (I) or pharmaceutically acceptable acid addition salts thereof and cardiotonic agents containing them as effective components.

DISCLOSURE OF THE INVENTION

The terms used for definition of letters in the above-mentioned formula by which the compounds of the present invention are represented are defined and exemplified in the following.

The wording "lower" refers to a group having 1 to 6 carbon atoms unless otherwise indicated.

The "lower alkyl group" refers to a straight- or branched-chain alkyl group such as methyl, ethyl, n-propyl, isopropyl, n-butyl, tert-butyl, n-pentyl, n-hexyl or the like.

The "lower alkoxy group" refers to a straight- or branched-chain alkoxy group such as methoxy, ethoxy, n-propoxy, isopropoxy, n-butoxy, tert-butoxy, n-pentyloxy, n-hexyloxy or the like.

The "halogen atom" may be fluorine, chlorine, bromine or iodine atom.

The compound according to the present invention is for example as follows:

2-[1-[2-Hydroxy-2-phenylethyl]-1,2,5,6-tetrahydropyrid-4-yl]-4H,6H-1,3,4-thiadiazin-5-one 2-[1-[2-Hydroxy-2-(2-methylphenyl)ethyl]-1,2,5,6-tetrahydropyrid-4-yl]-4H,6H-1,3,4-thiadiazin-5-one 2-[1-[2-Hydroxy-2-(3-methylphenyl)ethyl]-1,2,5,6-tetrahydropyrid-4-yl]-4H,6H-1,3,4-thiadiazin-5-one 2-[1-[2-Hydroxy-2-(4-methylphenyl)ethyl]-1,2,5,6-tetrahydropyrid-4-yl]-4H,6H-1,3,4-thiadiazin-5-one 2-[1-[2-Hydroxy-2-(2,4-dimethylphenyl)ethyl]-1,2,5,6-tetrahydropyrid-4-yl]-4H,6H-1,3,4-thiadiazin-5-one 2-[1-[2-Hydroxy-2-(4-isopropylphenyl)ethyl]-1,2,5,6-tetrahydropyrid-4-yl]-4H,6H-1,3,4-thiadiazin-5-one 2-[1-[2-(4-Fluorophenyl)-2-hydroxyethyl]-1,2,5,6-tetrahydropyrid-4-yl]-4H,6H-1,3,4-thiadiazin-5-one 2-[1-[2-(2-Chlorophenyl)-2-hydroxyethyl]-1,2,5,6-tetrahydropyrid-4-yl]-4H,6H-1,3,4-thiadiazin-5-one 2-[1-[2-(3-Chlorophenyl)-2-hydroxyethyl]-1,2,5,6-tetrahydropyrid-4-yl]-4H,6H-1,3,4-thiadiazin-5-one 2-[1-[2-(4-Chlorophenyl)-2-hydroxyethyl]-1,2,5,6-tetrahydropyrid-4-yl]-4H,6H-1,3,4-thiadiazin-5-one 2-[1-[2-(2, 4-Dichlorophenyl)-2-hydroxyethyl]-1,2,5,6-tetrahydropyrid-4-yl]-4H,6H-1,3,4-thiadiazin-5-one 2-[1-[2-(3,4-Dichlorophenyl)-2-hydroxyethyl]-1,2,5,6-tetrahydropyrid-4-yl]-4H,6H-1,3,4-thiadiazin-5-one 2-[1-[2-Hydroxy-2-(2-hydroxyphenyl)ethyl]-1,2,5,6-tetrahydropyrid-4-yl]-4H,6H-1,3,4-thiadiazin-5-one 2-[1-[2-Hydroxy-2-(3-hydroxyphenyl)ethyl]-1,2,5,6-tetrahydropyrid-4-yl]-4H,6H-1,3,4-thiadiazin-5-one 2-[1-[2-Hydroxy-2-(4-hydroxyphenyl)ethyl]-1,2,5.6-tetrahydropyrid-4-yl]-4H,6H-1,3,4-thiadiazin-5-one 2-[1-[2-Hydroxy-2-(2-methoxyphenyl)ethyl]-1,2,5,6-tetrahydropyrid-4-yl]-4H,6H-1,3,4-thiadiazin-5-one 2-[1-[2-Hydroxy-2-(3-methoxyphenyl)ethyl]-1,2,5,6-tetrahydropyrid-4-yl]-4H,6H-1,3,4-thiadiazin-5-one 2-[1-[2-Hydroxy-2-(4-methoxyphenyl)ethyl]-1,2,5,6-tetrahydropyrid-4-yl]-4H,6H-1,3,4-thiadiazin-5-one
2-[1-[2-Hydroxy-2-(2,5-dimethoxyphenyl)ethyl]-1,2,5,6-tetrahydro-pyrid-4-yl]-4H,6H-1,3,4-thiadiazin-5-one
2-[1-[2-Hydroxy-2-[3,4-(methylenedioxy)phenyl]ethyl]-1,2,5,6-tetrahydropyrid-4-yl]-4H,6H-1,3,4-thiadiazin-5-one
2-[1-[2-Hydroxy-2-(2-nitrophenyl)ethyl]-1,2,5,6-tetrahydropyrid-4-yl]-4H,6H-1,3,4-thiadiazin-5-one
2-[1-[2-Hydroxy-2-(3-nitrophenyl)ethyl]-1,2,5,6-tetrahydropyrid-4-yl]-4H,6H-1,3,4-thiadiazin-5-one
2-[1-[2-Hydroxy-2-(4-nitrophenyl)ethyl]-1,2,5,6-tetrahydropyrid-4-yl]-4H,6H-1,3,4-thiadiazin-5-one
2-[1-[2-(4-Aminophenyl)-2-hydroxyethyl]-1,2,5,6-tetrahydropyrid-4-yl]-4H,6H-1,3,4-thiadiazin-5-one
2-[1-[2-(4-Cyanophenyl)-2-hydroxyethyl]-1,2,8,6-tetrahydropyrid-4-yl]-4H,6H-1,3,4-thiadiazin-5-one
2-[1-[2-Hydroxy-2-[2-(trifluoromethyl)phenyl]ethyl]-1,2,5,6-tetrahydropyrid-4-yl]-4H,6H-1,3,4-thiadiazin-5-one
2-[1-[2-Hydroxy-2-[3-(trifloromethyl)phenyl]ethyl]-1,2,5,6-tetrahydropyrid-4-yl]-4H,6H-1,3,4-thiadiazin-5-one
2-[1-[2-(2-Chlorophenyl)-2-hydroxyethyl]-1,2,5,6-tetrahydropyrid-4-yl]-4-methyl-4H,6H-1,3,4-thiadiazin-5-one
2-[1-[2-Hydroxy-2-(4-methoxyphenyl)ethyl]-1,2,5,6-tetrahydropyrid-4-yl]-4-methyl-4H,6H-1,3,4-thiadiazin-5-one
2-[1-[2-Hydroxy-2-(4-methylphenyl)ethyl]-1,2,5,6-tetrahydropyrid-4-yl]-6-methyl-4H,6H-1,3,4-thiadiazin-5-one
2-[1-[2-Hydroxy-2-(4-methylphenyl)ethyl]-1,2,5,6-tetrahydropyrid-4-yl]-6,6-dimethyl-4H,6H-1,3,4-thiadiazin-5-one
6-Ethyl-2-[1-[2-hydroxy-2-(4-methylphenyl)ethyl]-1,2,5,6-tetrahydro-pyrid-4-yl]-4H,6H-1,3,4-thiadiazin-5-one
2-[1-[2-(2-Chlorophenyl)-2-hydroxyethyl]-1,2,5,6-tetrahydropyrid-4-yl]-6-methyl-4H,6H-1,3,4-thiadiazin-5-one
2-[1-[2-(4-Chlorophenyl)-2-hydroxyethyl]-1,2,5,6-tetrahydropyrid-4-yl]-6-methyl-4H,6H-1,3,4-thiadiazin-5-one
2-[1-[2-(4-Chlorophenyl)-2-hydroxyethyl]-1,2,5,6-tetrahydropyrid-4-yl]-6,6-dimethyl-4H,6H-1,3,4-thiadiazin-5-one
2-[1-[2-(2-Chlorophenyl)-2-hydroxyethyl]-1,2,5,6-tetrahydropyrid-4-yl]-6-ethyl-4H,6H-1,3,4-thiadiazin-5-one
2-[1-[2-(4-Chlorophenyl)-2-hydroxyethyl]-1,2,5,6-tetrahydropyrid-4-yl]-6-ethyl-4H,6H-1,3,4-thiadiazin-5-one
2-[1-[2-Hydroxy-2-(4-methoxyphenyl)ethyl]-1,2,5,6-tetrahydropyrid-4-yl]-6-methyl-4H,6H-1,3,4-thiadiazin-5-one
2-[1-[2-Hydroxy-2-(4-methoxyphenyl)ethyl]-1,2,5,6-tetrahydropyrid-4-yl]-6,6-dimethyl-4H,6H-1,3,4-thiadiazin-5-one
6-Ethyl-2-[1-[2-hydroxy-2-(4-methoxyphenyl) ethyl]-1,2,5,6-tetrahydro-pyrid-4-yl]-4H,6H-1,3,4-thiadiazin-5-one
2-[2-[2-Hydroxy-2-(4-nitrophenyl) ethyl]-1,2,5,6-tetrahydropyrid-4-yl]-6-methyl-4H,6H-1,3,4-thiadiazin-5-one
2-[1-[2-Isopropoxy-2-(4-methoxyphenyl)ethyl]-1,2,5,6-tetrahydropyrid-4-yl]-4H,6H-1,3,4-thiadiazin-5-one
2-[1-[2-Methoxy-2-(4-methoxyphenyl)ethyl]-1,2,5,6-tetrahydropyrid-4-yl]-4H,6H-1,3,4-thiadiazin-5-one
5-[1-(2-Hydroxy-2-phenylethyl)-1,2,5,6-tetrahydropyrid-4-yl]-3H,6H-1,3,4-thiadiazin-2-one
5-[1-[2-Hydroxy-2-(4-methylphenyl)ethyl]-1,2,5,6-tetrahydropyrid-4-yl]-3H,6H-1,3,4-thiadiazin-2-one
5-[1-[2-(4-Fluorophenyl)-2-hydroxyethyl]-1,2,5,6-tetrahydropyrid-4-yl]-3H,6H-1,3,4-thiadiazin-2-one
5-[1-[2-(2-Chlorophenyl)-2-hydroxyethyl]-1,2,5,6-tetrahydropyrid-4-yl]-3H,6H-1,3,4-thiadiazin-2-one
5-[1-[2-(4-Chlorophenyl)-2-hydroxyethyl]-1,2,5,6-tetrahydropyrid-4-yl]-3H,6H-1,3,4-thiadiazin-2-one
5-[1-[2-Hydroxy-2-(3-hydroxyphenyl)ethyl]-1,2,5,6-tetrahydropyrid-4-yl]-3H,6H-1,3, 4-thiadiazin-2-one
5-[1-[2-Hydroxy-2-(4-methoxyphenyl)ethyl]-1,2,5,6-tetrahydropyrid-4-yl]-3H,6H-1,3,4-thiadiazin-2-one
5-[1-[2(4-nitrophenyl)ethyl]-1,2,5,6-tetrahydropyrid-4-y]-3H,6H-1,3,4-thiadiazin-2-one
5-[1-[2-(4-Cyanophenyl)-2-hydroxyethyl]-1,2,5,6-tetrahydropyrid-4-yl]-3H,6H-1,3,4-thiadiazin-2-one
5-[1-[2-Hydroxy-2-[3-(trifluoromethyl)phenyl]ethyl]-1,2,5,6-tetrahydropyrid-4-yl]-3H,6H-1,3,4-thiadiazin-2-one
5-[1-[2-Hydroxy-2-(2-naphthyl)ethyl]-1,2,5,6-tetrahydropyrid-4-yl]-3H,6H-1,3,4-thiadiazin-2-one
5-[1-[2-Methoxy-2-(4-nitrophenyl)ethyl]-1,2,5,6-tetrahydropyrid-4-yl]-3H,6H-1,3,4-thiadiazin-2-one
4,5-Dihydro-3-[1-(2-hydroxy-2-phenylethyl)-1,2,5,6-tetrahydropyrid-4-yl]-1,2,4-triazin-6(1H)-one
4,5-Dihydro-3-[1-[2-hydroxy-2-(4-methylphenyl)ethyl]-1,2,5,6-tetrahydropyrid-4-yl]-1,2,4-triazin-6(1H)-one
3-[1-[2-(4-Fluorophenyl)-2-hydroxyethyl]-1,2,5,6-tetrahydropyrid-4-yl]-4,5-dihydro-1,2,4-triazin-6(1H)-one
3-[1-[2-(4-Chlorophenyl)-2-hydroxyethyl]-1,2,5,6-tetrahydropyrid-4-yl]-4,5-dihydro-1,2,4-triazin-6(1H)-one
4,5-Dihydro-3-[1-[2-hydroxy-2-(4-hydroxyphenyl)ethyl]-1,2,5,6-tetrahydropyrid-4-yl]-1,2,4-triazin-6(1H)-one
4,5-Dihydro-3-[1-[2-hydroxy-2-(4-methoxyphenyl)ethyl]-1,2,5,6-tetrahydropyrid-4-yl]-1,2,4-triazin-6(1H)-one
4,5-Dihydro-3-[1-[2-hydroxy-2-[3,4-(methylenedioxy)phenyl]ethyl]-1,2,5,6-tetrahydropyrid-4-yl]-1,2,4-triazin-6(1H)-one
4,5-Dihydro-3-[1-[2-hydroxy-2-(2-nitrophenyl)ethyl]-1,2,5,6-tetrahydropyrid-4-yl]-1,2,4-triazin-6(1H)-one
4,5-Dihydro-3-[1-[2-hydroxy-2-(3-nitrophenyl)ethyl]-1,2,5,6-tetrahydropyrid-4-yl]-1,2,4-triazin-6(1H)-one
4,5-Dihydro-3-[1-[2-hydroxy-2-(4-nitrophenyl)ethyl]-1,2,5,6-tetrahydropyrid-4-yl]-1,2,4-triazin-6(1H)-one
3-[1-[2-(4-Cyanophenyl)-2-hydroxyethyl]-1,2,5,6-tetrahydropyrid-4-y1]-4,5-dihydro-1,2,4-triazin-6(1H)-one
4,5-Dihydro-3-[1-[2-hydroxy-2-[2-(trifloromethyl)phenyl]ethyl]-1,2,5,6-tetrahydropyrid-4-yl]-1,2,4-triazin-6(1H)-one
3-[1-[2-(4-Aminophenyl)-2-hydroxyethyl]-1,2,5,6-tetrahydropyrid-4-yl]-4,5-dihydro-1,2,4-triazin-6(1H)-one
3-[1-[2-(4-Chlorophenyl)-2-methoxyethyl]-1,2,5,6-tetrahydropyrid-4-yl]-4,5-dihydro-1,2,4-triazin-6(1H)-one
4,5-Dihydro-3-[1-[2-methoxy-2-(4-nitrophenyl)ethyl]-1,2,5,6-tetrahydropyrid-4-yl]-1,2,4-triazin-6(1H)-one
4,5-Dihydro-6-[1-[2-hydroxy-2-phenylethyl]-1,2,5,6-tetrahydropyrid-4-yl]pyridazin-3(2H)-one
4,5-Dihydro-6-[1-[2-hydroxy-2-(2-methylphenyl)ethyl]-1,2,5,6-tetrahydropyrid-4-yl]pyridazin-3(2H)-one
6-[1-[2-(4-Fluorophenyl)-2-hydroxyethyl]-1,2,5,6-tetrahydropyrid-4-yl]-4,5-dihydropyridazin-3(2H)-one
6-[1-[2-(2-Chlorophenyl)-2-hydroxyethyl]-1,2,5,6-tetrahydropyrid-4-yl]-4,5-dihydropyridazin-3(2H)-one
4,5-Dihydro-6-[1-[2-hydroxy-2-(4-methoxyphenyl)ethyl]-1,2,5,6-tetrahydropyrid-4-yl]pyridazin-3(2H)-one
4,5-Dihydro-6-[1-[2-hydroxy-2-(4-nitrophenyl)ethyl]-1,2,5,6-tetrahydropyrid-4-yl]pyridazin-3(2H)-one
6-[1-[2-(4-Cyanophenyl)-2-hydroxyethyl]-1,2,5,6-tetrahydropyrid-4-yl]-4,5-dihydropyridazin-3(2H)-one
4,5-Dihydro-6-[1-[2-hydroxy-2-[2-(trifluoromethyl)phenyl]ethyl]-1,2,5,6-tetrahydropyrid-4-yl]pyridazin-3(2H)-one
6-[1-[2-(4-Chlorophenyl)-2-methoxyethyl]-1,2,5,6-tetrahydropyrid-4-yl]-4,5-dihydropyridazin-3(2H)-one Preferably, the group $R_1$ in the formula (I) is hydrogen atom and A–E is —S—$CH_2$—, —$CH_2$—S—, —NH—$CH_2$— or —$CH_2CH_2$—.

The compound of the present invention has asymmetric carbon atoms in its structure. It is to be understood that isomers due to such asymmetric carbon atom or combination (racemate) of any of the isomers are included in the category of the compound (I).

The compounds of the present invention represented by the formula (I) may be prepared by, for example, the following procedure.

The compound of the formula (II) was reacted with an equivalent mole or more of substituted or unsubstituted phenacyl bromide (compound of the formula III) in lower alcohol such as methanol, ethanol or isopropanol, dichloroethane or toluene at room temperature for one day or for 1 to 8 hours under reflux with heating to obtain pyridinium salt (hereinafter referred to as intermediate). This intermediate is a novel compound. The obtained intermediate, which is so pure as to be directly usable for a next process, may be further purified as needs demand by a normal purification method such as recrystallization from methanol, ethanol or absolute ethanol or column chromatography.

The intermediate obtained in the above-mentioned process is dissolved in lower alcohol such as methanol, ethanol or isopropanol, water or mixture thereof and gradually added with equivalent to 15 fold molar amount of reducing agent such as sodium borohydride under cooling and then reacted at room temperature for 1 to 24 hours, thereby preparing the compound of the formula (I) according to the present invention (see the following reaction formulae). The compounds of the formula (I) where R is lower alkyl can be prepared by reacting the compound of the formula (I) where R is hydrogen atom as starting material in lower alcohol under the presence of strong acid such as concentrated sulfuric acid, concentrated hydrochloric acid, p-toluenesulfonic acid at room temperature to reflux for one to 8 hours. If necessary, such reaction may be carried out in a mixed solution added with benzene.

The compounds of the present invention can be purified by the normal purification method such as that used for the above-mentioned intermediate.

Reaction Formula

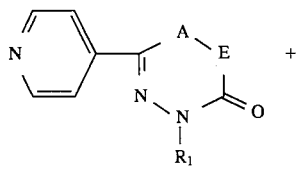

Formula II

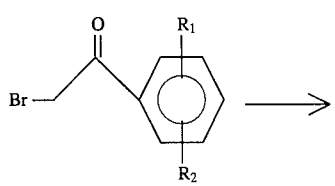

Formula III

-continued
Reaction Formula

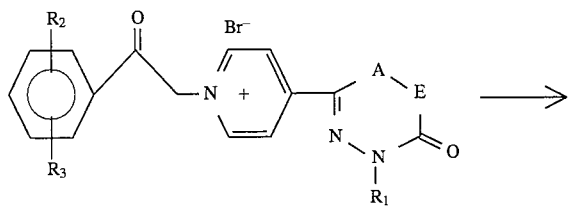

Formula IV: Intermediate

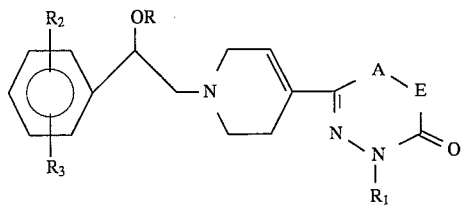

Formula I: Compound of the invention wherein R, $R_1$, $R_2$, $R_3$ and A–E are as defined above.

According to the above-mentioned procedure, the compounds of the formula (I) are ordinary obtained as racemate which may be mechanically or chemically divided into optical antipodes thereof by known process.

The compound of the formula (I) may be converted into a pharmaceutically acceptable salt by using an appropriate acid. The appropriate acids which can be used include, for example, inorganic acids such as hydrochloric, sulfuric, hydrobromic, nitric or phosphoric acid, and organic acids such as acetic, oxalic, propionic, glycolic, lactic, pyruvic, malonic, succinic, maleic, fumaric, malic, tartaric, citric, benzoic, cinnamic, methanesulfonic, benzenesulfonic, p-toluenesulfonic or salicylic acid.

The compound of the formula (II) which is the starting material in the above-mentioned process is a known compound and can be prepared according to a process described in Japanese Patent Publication (Kokoku) No.61-53350 or Japanese Patent Provisional Publication (Kokai) No. 57-2284 or 58-131981.

The pharmacological effects of the compound of the present invention represented by the formula (I) will now be described:

Nos. of the compounds in the pharmacological tests 1 and 2 correspond to those in Examples referred to hereinafter.

Pharmacological Test 1

A heart was removed from a male Hartley guinea pig (having a body weight of about 400 g or so) and a right atrium and papillary muscles of a right ventricle were separated from the removed heart. These preparations were suspended in 15 ml of Magnus' bath under load of 0.5 g (papillary muscles) or 1.0 g (right atria). Contraction of papillary muscles upon electric stimulation (1 Hz, 5 msec, 1.5×threshold voltage) and spontaneous contraction of the right atria were recorded through a transducer (manufactured by Orientec, T7-8-240) by a polygraph system (manufactured by NIHONKOHDEN, RMP-6008 and WT-685G).

Krebs-Henseleit solution was used as nutritive liquid bubbled with mixed gases of 95% $O_2$ with 5% $CO_2$ at 30° C. The samples were injected into bathes at a concentration of $3 \times 10^{-5}$M. The obtained results are shown in Table 1. The value of inotropic effect is a percentage of increment of contractile force by samples when that by isoprotelenol ($1 \times 10^{-8}$M) is considered to be 100%. The value of chronotropic effect is a percentage of atrial rate after the injection of samples when the atrial rate before the injection is considered to be 100%.

TABLE 1

| Compound No. | Inotropic Effect | Chronotropic Effect |
|---|---|---|
| 1 | 55.7 | 87.6 |
| 7 | 54.0 | 95.2 |
| 8 | 50.4 | 89.0 |
| 12 | 51.0 | 93.8 |
| 13 | 72.2 | 93.4 |
| 14 | 26.3 | 73.5 |
| 17 | 45.0 | 85.8 |
| 18 | 52.2 | 97.8 |
| 20 | 65.7 | 87.5 |
| 21 | 92.6 | 84.5 |
| 22 | 30.4 | 76.7 |
| 25 | 58.5 | 65.2 |
| 27 | 63.1 | 98.7 |
| 29 | 79.3 | 101.1 |
| 30 | 113.9 | 100.4 |
| 31 | 74.7 | 90.4 |
| 32 | 63.9 | 93.1 |
| 34 | 49.9 | 98.1 |
| 35 | 63.5 | 90.7 |
| 39 | 28.3 | 75.7 |
| 40 | 35.3 | 98.1 |
| 42 | 71.0 | 85.9 |
| 43 | 57.2 | 85.2 |
| 44 | 39.9 | 100.8 |
| 45 | 99.5 | 79.1 |
| 46 | 61.9 | 81.6 |
| 47 | 81.4 | 78.2 |
| 48 | 45.4 | 77.7 |
| 49 | 27.7 | 87.6 |
| 50 | 38.9 | 98.6 |
| 51 | 36.8 | 91.4 |
| 53 | 102.9 | 87.8 |
| 54 | 25.2 | 97.3 |
| 57 | 46.8 | 94.9 |
| 60 | 43.8 | 92.6 |
| 64 | 23.8 | 93.0 |
| 69 | 28.6 | 79.7 |
| 70 | 56.0 | 99.2 |
| 71 | 25.3 | 98.7 |
| a | 22.2 | 158.8 |
| b | 36.2 | 116.9 |
| c | 7.3 | 110.0 |
| d | 4.6 | 112.0 |

(unit: %)

As is clear from the above-mentioned test results, the compounds of the present invention selectively increase contractile force of cardiac muscles without increasing heart rate and therefore is useful as a cardiotonic agent for cure and prevention of acute and chronic heart failure.

The compounds a to d in Table 1 are typical examples of the compounds of the formula (II) (the starting materials of the present invention) and are as follows:

a: 2-(4-Pyridyl)-4H,6H-1,3,4-thiadiazin-5-one (typical compound disclosed in Japanese Patent Provisional Publication (Kokai) No. 58-131981)

b: 5-(4-Pyridyl)-3H,6H-1,3,4-thiadiazin-2-one (typical compound disclosed in Japanese Patent Provisional Publication (Kokai) No.58-131981)

c: 4,5-Dihydro-6-(4-pyridyl)-pyridazin-3(2H)-one (typical compound disclosed in Japanese Patent Publication (Kokoku) No. 61-53350)

d: 4,5-Dihydro-3-(4-pyridyl)-1,2,4-triazin-6(1H)-one (typical compounds disclosed in Japanese Patent Provisional Publication (Kokai) No. 58-131981)

Pharmacological Test 2

The acute toxicity was determined by administrating the sample compound, which was dissolved by physiological saline solution, in the tail vein of ddY mice (5-weeks-old, having a body weight of 25 to 28 g) and $LD_{50}$ was obtained by the up-and-down method. The obtained results are shown in Table 2.

TABLE 2

| Compound | Acute Toxicity (mg/kg) |
|---|---|
| hydrochloride of compound 13 | 101 |
| hydrochloride of compound 20 | 173 |
| hydrochloride of compound 21 | 226 |
| hydrochloride of compound 25 | 135 |
| hydrochloride of compound 30 | 160 |
| hydrochloride of compound 35 | 226 |
| hydrochloride of compound 60 | 226 |

The compounds of the present invention may be administered to human orally or subcutaneous, intramuscular or intravenous injection or other methods.

In oral administration, the compounds may be in the form of solids such as tablets, granules, powders, capsules or the like which may contain pharmaceutically acceptable additives such as binders, extenders and disintegrators and so on, e.g., saccharides and cellulose preparations. When used as liquids for oral administration, they may be in the form of mixture for internal use, suspensions, emulsions, syrups and so on. Alternatively, they may be in the forms of freeze-dried products which are to be dissolved upon use.

In injection, the compounds may be in the form of aqueous liquid, suspensions, oily or water-soluble emulsions which are usually prepared by dissolving or suspending the compounds in solvent such as sterile distilled water or physiological saline solution and which may be added with usually used solubilizers, stabilizers, preservatives and isotonicities as needs demand. Although the daily doses of these compounds may be varied according to the conditions, ages or weights of the subjects to be treated, the daily doses to adult humans (weights: 60 kg) may fall within the range of 6–600 mg and may be divided into two or three portions.

BEST MODE FOR CARRYING OUT THE INVENTION

[Preparations and Examples]

The present invention is more specifically illustrated with reference to the following preparations and examples. It is to be, however, noted that the present invention is not limited to the preparations and examples.

Preparation 1: Preparation of 1-[(4-methoxyphenyl)carbonylmethyl]-4-(4H,6H-1,3,4-thiadiazin-5-one-2-yl)pyridinium bromide (Intermediate 1)

2-(4-Pyridyl)-4H,6H-1,3,4-thiadiazin-5-one (1.88 g, 9.74 mmol) and 4'-methoxyphenacyl bromide (2.23 g, 9.74 mmol) were dissolved in absolute ethanol (40 ml) and stirred at room temperature for one day. The resulting precipitate was collected by filtration and washed with absolute ethanol to obtain the titled compound (3.84 g) as yellow powder.

Yield: 93%

Melting Point: 174°–178° C. (dec.)

In accordance with the procedure of the Preparation 1, the intermediates of the formula IV shown in Tables 3 and 4 were obtained from corresponding starting materials.

TABLE 3

Formula IV

| Intermediate | R₁ | R₂ | R₃ | A-E | Yield (%) | Melting Point (°C.) | Appearance |
|---|---|---|---|---|---|---|---|
| 2 | H | H | H | —S—CH₂— | 98.7 | >182 (dec.) | yellow-white powder |
| 3 | H | 4—OCH₃ | H | —S—CH(CH₃)— | 92.9 | 172.0–175.0 (dec.) | opaline powder |
| 4 | H | 4—OCH₃ | H | —S—CH(C₂H₅)— | 92.9 | >147.5 (dec.) | yellow powder |
| 5 | H | 4—OCH₃ | H | —S—C(CH₃)₂— | 93.6 | >145 (dec.) | yellow powder |
| 6 | H | 2—OCH₃ | H | —S—CH₂— | 91 | >250 (dec.) | light yellow powder |
| 7 | H | 3—OCH₃ | H | —S—CH₂— | 85 | 230–233 (dec.) | yellow powder |
| 8 | H | 2—OCH₃ | 5—OCH₃ | —S—CH₂— | 83 | >250 (dec.) | yellow plate |
| 9 | H | 2—Cl | H | —S—CH₂— | 63 | 258–260 (dec.) | yellow powder |
| 10 | H | 2—Cl | H | —S—CH(CH₃)— | 85 | — | yellow-brown gum |
| 11 | H | 2—Cl | H | —S—CH(C₂H₅)— | 94.6 | 236–237 (dec.) | yellow-white powder |
| 12 | H | 3—Cl | H | —S—CH₂— | 87 | — | gum |
| 13 | H | 4—Cl | H | —S—CH₂— | 98 | 202–207 (dec.) | yellow column |
| 14 | H | 4—Cl | H | —S—CH(CH₃)— | 93 | >171 (dec.) | yellow-white powder |
| 15 | H | 4—Cl | H | —S—CH(C₂H₅)— | 98.5 | >145 (dec.) | yellow-white powder |
| 16 | H | 4—Cl | H | —S—C(CH₃)₂— | 95.2 | >167 (dec.) | light yellow powder |

TABLE 4

| Intermediate | R₁ | R₂ | R₃ | A—E | Yield (%) | Melting Point (°C.) | Appearance |
|---|---|---|---|---|---|---|---|
| 17 | H | 2-Cl | 4-Cl | —S—CH₂— | 74 | 225–227 (dec.) | ocher yellow powder |
| 18 | H | 3-Cl | 4-Cl | —S—CH₂— | 83 | 223–225 (dec.) | yellow powder |
| 19 | H | 2-CH₃ | H | —S—CH₂— | 88 | 246–248 (dec.) | light green plate |
| 20 | H | 3-CH₃ | H | —S—CH₂— | 80 | 162–166 (dec.) | yellow powder |
| 21 | H | 4-CH₃ | H | —S—CH₂— | 87 | 193–196 (dec.) | yellow plate |
| 22 | H | 4-CH₃ | H | —S—CH(CH₃)— | 92.6 | >141 (dec.) | light yellow powder |
| 23 | H | 4-CH₃ | H | —S—CH(C₂H₅)— | 94.9 | >137 (dec.) | yellow powder |
| 24 | H | 4-CH₃ | H | —S—C(CH₃)₂— | 81.8 | >152 (dec.) | yellow powder |
| 25 | H | 2-CH₃ | 4-CH₃ | —S—CH₂— | 70 | — | gum |
| 26 | H | 2-OH | H | —S—CH₂— | 85 | 228–230 (dec.) | brown powder |
| 27 | H | 3-OH | H | —S—CH₂— | 91 | >250 (dec.) | yellow powder |
| 28 | H | 4-OH | H | —S—CH₂— | 89 | — | yellow powder |
| 29 | H | 2-NO₂ | H | —S—CH₂— | 77 | 242 (dec.) | yellow powder |
| 30 | H | 3-NO₂ | H | —S—CH₂— | 93 | 111–120 (dec.) | yellow powder |
| 31 | H | 4-NO₂ | H | —S—CH₂— | 30 | — | gum |
| 63 | H | 4-NH₂ | H | —S—CH₂— | 97.8 | 217.0–219.0 (dec.) | orange powder |
| 32 | H | 3-O—CH₂—O-4 | | —S—CH₂— | 80 | 245–249 (dec.) | light brown powder |
| 33 | H | 2-CF₃ | H | —S—CH₂— | 45 | 240–245 (dec.) | yellow powder |
| 34 | H | 3-CF₃ | H | —S—CH₂— | 82 | — | gum |
| 35 | H | 4-F | H | —S—CH₂— | 94 | 156–158 (dec.) | yellow powder |
| 36 | H | 4-CH(CH₃)₂ | H | —S—CH₂— | 63 | — | gum |
| 37 | CH₃ | 4-OCH₃ | H | —S—CH₂— | 67 | 237–243 (dec.) | yellow powder |
| 38 | CH₃ | 2-Cl | H | —S—CH₂— | 67 | 200–202 (dec.) | yellow powder |

Preparation 2: Preparation of 1-[(4-methoxyphenyl)carbonylmethyl]-4-(3H,6H-1,3,4-thiadiazin-2-one-5-yl)pyridinium bromide (Intermediate 39)

5-(4-Pyridyl)-3H,6H-1,3,4-thiadiazin-2-one (386 mg, 2 mmol) and 4'-methoxyphenacyl bromide (550 mg, 2.4 mmol) were dissolved in absolute ethanol (6 ml), refluxed for three hours and then stirred at room temperature overnight. The resulting precipitate was collected by filtration and washed with absolute ethanol to obtain the titled compound (814 mg) as light brown powder.

Yield: 96.4%

Melting Point: 223.5°–224° C. (dec.)

In accordance with the procedure of the Preparation 2, the intermediates of the formula IV shown in Table 5 were obtained from corresponding starting materials.

TABLE 5

| Intermediate | $R_1$ | $R_2$ | $R_3$ | A—E | Yield (%) | Melting Point (°C.) | Appearance |
|---|---|---|---|---|---|---|---|
| 40 | H | H | H | —CH$_2$—S— | 98 | 224–224.5 (dec.) | yellow powder |
| 41 | H | 2-Cl | H | —CH$_2$—S— | 94 | 226.3 (dec.) | light brown powder |
| 42 | H | 4-Cl | H | —CH$_2$—S— | 99.1 | >153 (dec.) | light yellow-brown powder |
| 43 | H | 4-CH$_3$ | H | —CH$_2$—S— | 92.1 | >153 (dec.) | light brown powder |
| 44 | H | 3-OH | H | —CH$_2$—S— | 93.6 | 217 (dec.) | light brown powder |
| 45 | H | 4-NO$_2$ | H | —CH$_2$—S— | 90.3 | — | brown hygroscopic matter |
| 46 | H | 4-F | H | —CH$_2$—S— | 97.6 | >152.5 (dec.) | light orange powder |
| 47 | H | 4-CN | H | —CH$_2$—S— | 88.5 | — | hygroscopic matter |
| 48 | H | 3-CF$_3$ | H | —CH$_2$—S— | 92.3 | — | yellow-brown gum |
| 69 | H | 3-CH=CH—CH=CH-4 | | —CH$_2$—S— | 97.5 | 244.5 (dec.) | yellow-brown powder |

Preparation 3: Preparation of 1-[(4-methoxyphenyl)carbonylmethyl]-4-(4,5-dihydropyridazin-3(2H)-one-6-yl)pyridinium bromide (Intermediate 49)

4,5-Dihydro-6-(4-pyridyl)-pyridazin-3(2H)-one (175 mg, 1 mmol) and 4'-methoxyphenacyl bromide (252 mg, 1.1 mmol) were dissolved in absolute ethanol (5 ml), refluxed for two hours and then stirred at room temperature overnight. The resulting precipitate was collected by filtration and washed with absolute ethanol to obtain the titled compound (350 mg) as brown columns.

Yield: 87%

Melting Point: 250°–255° C. (dec.)

In accordance with the procedure of the Preparation 3, intermediates of the formula IV shown in Table 6 were obtained from corresponding starting materials.

washed with absolute ethanol to obtain the titled compound (374 mg) as yellow-brown powder.

Yield: 92%

Melting Point: 220°–225° C. (dec.)

In accordance with the procedure of the Preparation 4, intermediates of the formula IV shown in Table 7 were obtained from corresponding starting materials.

TABLE 6

| Intermediate | $R_1$ | $R_2$ | $R_3$ | A—E | Yield (%) | Melting Point (°C.) | Appearance |
|---|---|---|---|---|---|---|---|
| 50 | H | 2-Cl | H | —CH$_2$CH$_2$— | 81 | 233–236 (dec.) | yellow powder |
| 51 | H | 4-F | H | —CH$_2$CH$_2$— | 89 | 190–196 (dec.) | yellow-brown powder |
| 52 | H | 2-CH$_3$ | H | —CH$_2$CH$_2$— | 75 | 226–229 (dec.) | yellow-brown powder |
| 53 | H | 4-NO$_2$ | H | —CH$_2$CH$_2$— | 75 | 239–241 (dec.) | brown powder |
| 54 | H | 2-CF$_3$ | H | —CH$_2$CH$_2$— | 74 | 237–238 (dec.) | yellow powder |
| 55 | H | H | H | —CH$_2$CH$_2$— | 64 | 150–154 (dec.) | yellow-brown powder |

Preparation 4: 1-[(4-Methoxyphenyl)carbonylmethyl]-4-(4,5-dihydro-1,2,4-triazin-6(1H)-one-3-yl)pyridinium bromide

TABLE 7

| Intermediate | $R_1$ | $R_2$ | $R_3$ | A—E | Yield (%) | Melting Point (°C.) | Appearance |
|---|---|---|---|---|---|---|---|
| 57 | H | 4-Cl | H | —NH—CH$_2$— | 84 | 264–266 (dec.) | yellow powder |
| 58 | H | 4-CH$_3$ | H | —NH—CH$_2$— | 84 | 277–281 (dec.) | yellow powder |
| 59 | H | 4-F | H | —NH—CH$_2$— | 96 | 200–203 (dec.) | yellow-brown powder |
| 60 | H | 4-NO$_2$ | H | —NH—CH$_2$— | 98 | 200–203 (dec.) | yellow-brown powder |
| 61 | H | 2-CF$_3$ | H | —NH—CH$_2$— | 81 | 223–228 (dec.) | yellow powder |
| 62 | H | H | H | —NH—CH$_2$— | 88 | 259–262 (dec.) | yellow-brown powder |
| 64 | H | 4-CN | H | —NH—CH$_2$— | 96 | 263–265 (dec.) | yellow powder |
| 65 | H | 4-NH$_2$ | H | —NH—CH$_2$— | 98 | >300 (dec.) | yellow-brown powder |
| 66 | H | 2-NO$_2$ | H | —NH—CH$_2$— | 66 | 223–226 (dec.) | yellow-brown powder |
| 67 | H | 3-NO$_2$ | H | —NH—CH$_2$— | 89 | 217–220 (dec.) | yellow powder |
| 68 | H | 3-O—CH$_2$—O-4 | | —NH—CH$_2$— | 94 | 235–238 (dec.) | yellow powder |
| 72 | H | 4-OH | H | —NH—CH$_2$— | 90 | 294–297 (dec.) | yellow powder |

(Intermediate, 56)

4,5-Dihydro-3-(4-pyridyl)-1,2,4-triazin-6(1H)-one (176 mg, 1 mmol) and 4'-methoxyphenacyl bromide (252 mg, 1.1 mmol) were dissolved in absolute ethanol (5 ml), refluxed for two hours and then stirred at room temperature for one day. The resulting precipitate was collected by filtration and

EXAMPLE 1

2-[1-[2-Hydroxy-2-(4-methoxyphenyl)ethyl]-1,2,5,6-tetrahydropyrid-4-yl]-4H,6H-1,3,4-thiadiazin-5-one (Compound 1)

1-[(4-Methoxyphenyl)carbonylmethyl]-4-(4H,6H-1,3,4-thiadiazin-5-one-2-yl)pyridinium bromide (3.84 g, 9.09 mmol) was dissolved in methanol-water (1:1 v/v %) (50 ml), gradually added with sodium borohydride (3.43 g, 90.9 mmol) under ice cooling and then stirred at room temperature overnight. The solvent was removed under reduced pressure. The residue was added with dichloromethane, then washed with water and dried over anhydrous magnesium sulfate. The solvent was removed to obtain the titled compound (2.44 g) as white crystals.

Yield: 70%

Melting Point: 197°–198° C. (recrystallization from acetone-methanol)

IR(KBr)cm$^{-1}$: 3454, 3217, 3096, 1671

NMR(CDCl$_3$-DMSO-d$_6$) δ: 2.50–2.70(6H, m), 3.20–3.50(2H, m), 3.29(2H, s), 3.80(3H, s), 4.15(1H, brs), 4.75(1H, m), 6.45(1H, s), 6.87(2H, d, J=8 Hz), 7.30(2H, d, J=8 Hz), 10.75(1H,s)

MS m/z: 347(M$^+$)

In accordance with the procedure of the Example 1, the following compounds were obtained from corresponding starting materials.

2-[1-[2-Hydroxy-2-(4-methoxyphenyl)ethyl]-1,2,5,6-tetrahydropyrid-4-yl]-6-methyl-4H,6H-1,3,4-thiadiazin-5-one (Compound 3)

Yield: 74.2%

Appearance: colorless needles (recrystallization from ethanol)

Melting Point: 182.5°–184.5° C.

IR(KBr)cm$^{-1}$: 3196, 3099, 1672

NMR(DMSO-d$_6$) δ: 1.28(3H, d, J=7 Hz), 2.40(2H, s), 2.44–2.65(4H, m), 3.22(2H, s), 3.59(1H, q, J=7 Hz), 3.73(3H, s), 4.68(1H, m), 4.92(1H, d, J=3.7 Hz), 6.38(1H, s), 6.86(2H, d, J=8.8 Hz), 7.26(2H, d, J=8.8 Hz), 11.37(1H, s)

MS m/z: 361(M$^+$)

6-Ethyl-2-[1-[2-hydroxy-2-(4-methoxyphenyl)ethyl]-1,2,5,6-tetrahydropyrid-4-yl]-4H,6H-1,3,4-thiadiazin-5-one (Compound 4)

Yield: 59.2%

Appearance: opaline needles (recrystallization from ethanol)

Melting Point: 148°–149° C. (dec.)

IR(KBr)cm$^{-1}$: 3188, 3104, 1664, 1612

NMR(DMSO-d$_6$) δ: 0.94(3H, t, J=7.3 Hz), 1.43(1H, m), 1.69(1H, m), 2.35–2.64(6H, m), 3.22(2H, s), 3.45(1H, m), 3.73(3H, s), 4.69(1H, m), 4.94(1H, d, J=3.7 Hz), 6.41(1H,s), 6.87(2H, d, J=8.4Hz), 7.26(2H, d, J=8.4 Hz), 11.39(1H, s)

MS m/z: 375(M$^+$)

2-[1-[2-Hydroxy-2-(4-methoxyphenyl)ethyl]-1,2,5,6-tetrahydropyrid-4-yl]6,6-dimethyl-4H,6H-1,3,4-thiadiazin-5-one (Compound 5)

Yield: 46.5%

Appearance: light yellow-brown granules (recrystallization from ethanol)

Melting Point: 179.5°–181.5° C. (dec.)

IR(KBr)cm$^{-1}$: 3231, 3196, 3091, 1658

NMR(DMSO-d$_6$) δ: 1.32(6H, s), 2.40(2H, s), 2.43–2.67(4H, m), 3.22(2H, s), 3.73(3H, s), 4.68(1H, m), 4.95(1H, d, J=4 Hz), 6.35(1H, s), 6.87(2H, d, J=8.4 Hz), 7.23(2H, d,J=8.4 Hz), 11.38(1H, s)

MS m/z: 375(M$^+$)

2-[1-(2-Hydroxy-2-phenylethyl)-1,2,5,6-tetrahydropyrid-4-yl]-4H,6H-1,3,4-thiadiazin-5-one (Compound 2)

Yield: 77.8%

Appearance: colorless plates (recrystallization from ethanol)

Melting Point: 179.5°–181.5° C. (dec.)

IR(KBr)cm$^{-1}$: 3176, 3085, 3018, 1666

NMR(DMSO-d$_6$) δ: 2.39(2H, s), 2.47–2.68(4H, m), 3.24(2H, d, J=2.9 Hz), 3.41 (2H, s), 4.74(1H, m), 5.05(1H, d, J=3.7 Hz), 6.40(1H, s), 7.20–7.36(5H, m), 11.37(1H, s)

MS m/z: 317 (M$^+$)

2-[1-[2-Hydroxy-2-(2-methoxyphenyl)ethyl]-1,2,5,6-tetrahydropyrid-4-yl]-4H,6H-1,3,4-thiadiazin-5-one (Compound 6)

Yield: 78%

Appearance: white powder (recrystallization from chloroform-methanol)

Melting Point: 194°–196° C. (dec.)

IR(KBr)cm$^{-1}$: 3443, 3167, 3079, 3008, 1671

NMR(DMSO-d$_6$) δ: 2.40(2H, s), 2.40–2.55(2H, m), 2.66(2H, s), 3.15–3.35(2H, m), 3.41(2H, s), 3.78(3H, s), 4.91(1H, d, J=4.4 Hz), 5.08(1H, brs), 6.42(1H, s), 6.90–6.95(2H, m), 7.20(1H, t, J=6.2 Hz), 7.42(1H, d, J=6.2 Hz), 11.39(1H, s)

MS m/z: 347 (M$^+$)

2-[1-[2-Hydroxy-2-(3-methoxyphenyl)ethyl]-1,2,5,6-tetrahydropyrid-4-yl]-4H,6H-1,3,4-thiadiazin-5-one (Compound 7)

Yield: 59%

Appearance: white powder (recrystallization from dichloromethane-hexane)

Melting Point: 152°–153° C. (dec.)

IR(KBr)cm$^{-1}$: 3178, 3087, 3016, 1667

NMR(DMSO-d$_6$) δ: 2.38(2H, s), 2.51–2.66(4H, m), 3.23(2H, s), 3.41(2H, s), 3.73(3H, s), 4.71(1H, brs), 5.05(1H, d, J=4 Hz), 6.40(1H, s), 6.78(1H, d, J=7.3 Hz), 6.91(2H, s+d, J=7.3 Hz), 7.21(1H, m), 11.37(1H, s)

MS m/z: 347 (M$^+$)

2-[1-[2-Hydroxy-2-(2,5-dimethoxyphenyl)ethyl]-1,2,5,6-tetrahydropyrid-4-yl]-4H,6H-1,3,4-thiadiazin-5-one (Compound 8)

Yield: 82%

Appearance: light yellow powder (recrystallization from dichloromethane-hexane)

Melting Point: 176°–178° C. (dec.)

IR(KBr)cm$^{-1}$: 3182, 3095, 1670

NMR(CDCl$_3$) δ:2.50–2.95(6H, m), 3.15–3.50(2H, m), 3.31(2H, s), 3.80(6H, s), 3.85(1H, brs), 5.15(1H, m), 6.50(1H, s), 6.80(2H, ABq, J=9 Hz), 7.15(1H, s), 9.05(1H, s)

MS m/z: 377 (M$^+$)

2-[1-[2-(2-Chlorophenyl)-2-hydroxyethyl]-1,2,5,6-tetrahydropyrid-4-yl]-4H,6H-1,3,4-thiadiazin-5-one (Compound 9)

Yield: 76%

Appearance: light pink powder (recrystallization from chloroform-methanol)

Melting Point: 193°–195° C. (dec.)

IR(KBr)cm$^{-1}$: 3433, 3168, 3075, 3009, 1664

NMR(DMSO-d$_6$) δ: 2.40(2H, s), 2.52–2.54(2H, m), 2.68(2H, m), 3.20–3.30 (2H, m), 3.41(2H, s), 5.10(1H, brs), 5.33(1H, d, J=4.4 Hz), 6.42(1H, s), 7.25–7.29(1H, m), 7.34–7.38(2H, m), 7.60(1H, d, J=5.9 Hz), 11.38(1H, s)

MS m/z: 352(M$^+$)

2-[1-[2-(2-Chlorophenyl)-2-hydroxyethyl]-1,2,5,6-tetrahydropyrid-4-yl]-6-ethyl-4H,6H-1,3,4-thiadiazin-5-one (Compound 11)

Yield: 89.3%

Appearance: white powder (recrystallization from ethanol)

Melting Point: 154.5°–156.5° C. (dec.)

IR(KBr)cm$^{-1}$: 3202, 1674

NMR(DMSO-d$_6$) δ: 0.94(3H, t, J=7.3 Hz), 1.43(1H, m), 1.70(1H, m), 2.30–12.74(6H, m), 3.27(2H, m), 3.46(1H, m), 5.12 (1H, m), 5.33(1H, d, J=4 Hz), 6.42(1H, s), 7.24–7.61(4H, m), 11.39(1H, s)

MS m/z: 379(M$^+$)

2-[1-[2-(3-Chlorophenyl)-2-hydroxyethyl]-1,2,5,6-tetrahydropyrid-4-yl]-4H,6H-1,3,4-thiadiazin-5-one (Compound 12)

Yield: 70%

Appearance: yellow powder (recrystallization from chloroform)

Melting Point: 195°–198° C. (dec.)

IR(KBr)cm$^{-1}$: 3459, 3179, 3080, 1659

NMR(DMSO-d$_6$) δ: 2.37(2H, s), 2.51–2.70(2H, m), 3.23(2H, s), 4.77(1H, brs), 5.26(1H, d, J=4.4 Hz), 6.40(1H, s), 7.26–7.36(4H, m), 7.40(1H, s), 11.39(1H, s)

MS m/z: 351 (M$^+$)

2-[1-[2-(4-Chlorophenyl)-2-hydroxyethyl]-1,2,5,6-tetrahydropyrid-4-yl]-4H,6H-1,3,4-thiadiazin-5-one (Compound 13)

Yield: 70%

Appearance: yellow powder (recrystallization from tetrahydrofuran)

Melting Point: 218°–20° C. (dec.)

IR(KBr)cm$^{-1}$: 3449, 3179, 3079, 1660

NMR(DMSO-d$_6$) δ: 2.38(2H, brs), 2.56–2.75(4H, m), 3.22(2H,s), 3.41(2H, s), 4.75–4.80(1H, brs), 5.20(1H, d, J=4 Hz), 6.39(1H, s), 7.36(4H, ABq, J=9 Hz), 11.37(1H, s)

MS m/z: 351 (M$^+$)

2-[1-[2-(4-Chlorophenyl)-2-hydroxyethyl]-1,2,5,6-tetrahydropyrid-4-yl]-6-methyl-4H,6H-1,3,4-thiadiazin-5-one (Compound 14)

Yield: 90.9%

Appearance: opaline particles (recrystallization from ethanol)

Melting Point: 179.5°–180.5° C. (dec.)

IR(KBr)cm$^{-1}$: 3359, 3063, 3018, 1662

NMR(DMSO-d$_6$) δ: 1.27(3H, d, J=7 Hz), 2.39(2H, s), 2.46–2.69(4H, m), 3.22 (2H, s), 3.60(1H, q, J=7 Hz), 4.74(1H, m), 5.18(1H, d, J=4 Hz), 6.39(1H, s), 7.33–7.39(4H, m), 11.38(1H, s)

MS m/z: 365 (M$^+$)

2-[1-[2-(4-Chlorophenyl)-2-hydroxyethyl]-1,2,5,6-tetrahydropyrid-4-yl]-6-ethyl-4H,6H-1,3,4-thiadiazin-5-one (Compound 15)

Yield: 90%

Appearance: opaline plates (recrystallization from ethanol)

Melting Point: 150.5°–153.5° C. (dec.)

IR(KBr)cm$^{-1}$: 3190, 3089, 1668

NMR(DMSO-d$_6$) δ: 0.94(3H, t, J=7.3 Hz), 1.43(1H, m), 1.69(1H, m), 2.31–2.67(6H, m), 3.22(2H, s), 3.45(1H, m), 4.74 (1H, m), 5.18(1H, d, J=4 Hz), 6.40(1H, s), 7.33–7.39(4H, m), 11.38(1H, s)

MS m/z: 379(M$^+$)

2-[1-[2-(4-Chlorophenyl)-2-hydroxyethyl]-1,2,5,6-tetrahydropyrid-4-yl]-6,6-dimethyl-4H,6H-1,3,4-thiadiazin-5-one (Compound 16)

Yield: 78.7%

Appearance: yellow powder (recrystallization from ethanol)

Melting Point: 190°–192.5° C. (dec.)

IR(KBr)cm$^{-1}$: 3454, 3237, 3089, 1655

NMR(DMSO-d$_6$) δ: 1.33(6H, s), 2.39(2H, s), 2.46–2.69(4H, m), 3.21(2H, s), 4.74(1H, m), 5.18(1H, d, J=4 Hz), 6.35(1H, s), 7.33–7.39(4H, m), 11.37(1H, s)

MS m/z: 379(M$^+$)

2-[1-[2-(2,4-Dichlorophenyl)-2-hydroxyethyl]-1,2,5,6-tetrahydropyrid-4-yl]-4H,6H-1,3,4-thiadiazin-5-one (Compound 17)

Yield: 64%

Appearance: yellow powder (recrystallization from chloroform)

Melting Point: 198°–01° C. (dec.)

IR(KBr)cm$^{-1}$: 3182, 3095, 3008, 1671

NMR (DMSO-d$_6$) δ: 2.39(2H, s), 2.51–2.55(2H, m), 2.67(2H, m), 3.23–3.30 (2H, m), 3.41 (2H, s), 5.08(1H, brs), 5.47(1H, d, J=4.4 Hz), 6.41(1H, brs), 7.44(1H, d, J=8.4 Hz), 7.53(1H, s), 7.60(1H, d, J=8.4 Hz), 11.39(1H, s)

MS m/z: 385 (M$^+$)

2-[1-[2-(3,4-Dichlorophenyl)-2-hydroxyethyl]-1,2,5,6-tetrahydropyrid-4-yl]-4H,6H-1,3,4-thiadiazin-5-one (Compound 18)

Yield: 51%

Appearance: yellow powder (recrystallization from chloroform-methanol)

Melting Point: 204°–207° C. (dec.)

IR(KBr)cm$^{-1}$: 3446, 3175, 3075, 1656

NMR(DMSO-d$_6$) δ: 2.37(2H, s), 2.52–2.67(4H, m), 3.22(2H, s), 3.41(2H, s), 4.76(1H, brs), 5.35(1H, s), 7.34(1H, d,J=8.4 Hz), 7.58(2H, dd, J=1.8 Hz, 8.4 Hz), 11.37(1H, s)

MS m/z: 385 (M$^+$)

2-[1-[2-Hydroxy-2-(2-methylphenyl)ethyl]-1,2,5,6-tetrahydropyrid-4-yl]-4H,6H-1,3,4-thiadiazin-5-one (Compound 19)

Yield: 73%

Appearance: white powder (recrystallization from chloroform-methanol)

Melting Point: 180°–182° C. (dec.)

IR(KBr)cm$^{-1}$: 3197, 3111, 1676

NMR(DMSO-d$_6$) δ: 2.29(3H, s), 2.40–2.60(4H, m), 2.65–2.67(2H, m), 3.20–3.30(2H, m), 3.41(2H, s), 4.97(2H, m), 6.41 (1H, s), 7.10–7.25(3H, m), 7.45(1H, d, J=7.3 Hz), 11.39 (1H, s)

MS m/z: 331 (M$^+$)

2-[1-[2-Hydroxy-2-(3-methylphenyl)ethyl]-1,2,5,6-tetrahydropyrid-4-yl]-4H,6H-1,3,4-thiadiazin-5-one (Compound 20)

Yield: 70%

Appearance: white powder (recrystallization from dichloromethanemethanol)

Melting Point: 183°–184° C. (dec.)

IR(KBr)cm$^{-1}$: 3458, 3176, 3076, 1663 NMR(CDCl$_3$-DMSO-d$_6$) δ: 2.35(3H, s), 2.60–2.70(5H, m), 2.90–3.00(1H, m), 3.20–3.30(2H+2H, M+s), 4.00(1H, brs), 4.77 (1H, t, J=6.8 Hz), 6.46(1H, s), 7.07–7.24 (4H, m), 9.92 (1H, s)

MS m/z: 331 (M$^+$)

2-[1-[2-Hydroxy-2-(4-methylphenyl)ethyl]-1,2,5,6-tetrahydropyrid-4-yl]-4H,6H-1,3,4-thiadiazin-5-one (Compound 21)

Yield: 33%

Appearance: white powder (recrystallization from tetrahydrofuran)

Melting Point: 205°–208° C. (dec.)

IR(KBr)cm$^{-1}$: 3453, 3179, 3080, 1663

NMR(DMSO-d$_6$) δ: 2.27(3H, s), 2.73(2H, s), 2.55–2.65(4H, m), 3.22(2H, s), 3.40(2H, s), 4.69(1H, brs), 4.97(1H, d,J=3.7 Hz), 6.39(1H, s), 7.11(2H, d, J=8 Hz), 7.22(2H, d, J=8 Hz), 11.38(1H, s)

MS m/z: 331 (M$^+$)

2-[1-[2-Hydroxy-2-(4-methylphenyl)ethyl]-1,2,5,6-tetrahydropyrid-4-yl]-6-methyl-4H,6H-1,3,4-thiadiazin-5-one (Compound 22)

Yield: 78.5%

Appearance: white powder (recrystallization from ethanol)

Melting Point: 174.5°–176.5° C. (dec.)

IR(KBr)cm$^{-1}$: 3191, 3090, 1671

NMR(DMSO-d$_6$) δ: 1.27(3H, d, J=7 Hz), 2.27(3H, s), 2.39 (2H, s), 2.45–2.65(4H, m), 3.22(2H, s), 3.60(1H, q, J=7 Hz), 4.69(1H, m), 4.95(1H, d, J=3.7 Hz), 6.38(1H, s), 7.11(2H, d, J=8.1 Hz), 7.22 (2H, d, J=8.1 Hz), 11.37(1H, s)

MS m/z: 345(M$^+$)

6-Ethyl-2-[1-[2-hydroxy-2-(4-methylphenyl)ethyl]-1,2,5,6-tetrahydropyrid-4-yl]-4H,6H-1,3,4-thiadiazin-5-one (Compound 23)

Yield: 80.2%

Appearance: white prisms (recrystallization from ethanol)

Melting Point: 160°–162° C. (dec.)

IR(KBr)cm$^{-1}$: 3189. 3086, 1633

NMR(DMSO-d$_6$) δ: 0.94(3H, t, J=7.3 Hz), 1.43(1H, m), 1.69(1H, m), 2.28(3H, s), 2.35–2.67(6H, m), 3.23(2H, s), 3.45(1H, m), 4.69(1H, m), 4.96(1H, d, J=4 Hz), 6.41(1H, s), 7.11 (2H, d, J=8.1 Hz), 7.22(2H, d, J=8.1 Hz), 11.38(1H,s)

MS m/z: 359(M$^+$)

2-[1-[2-Hydroxy-2-(4-methylphenyl)ethyl]-1,2,5,6-tetrahydropyrid-4-yl]-6,6-dimethyl-4H,6H-1,3,4-thiadiazin-5-one (Compound 24)

Yield: 47.7%

Appearance: light yellow plates (recrystallization from ethanol)

Melting Point: 182°–184° C. (dec.)

IR(KBr)cm$^{-1}$: 3235, 3198, 3089, 1656

NMR(DMSO-d$_6$) δ: 1.33(6H, s), 2.27(3H, s), 2.40(2H, s), 2.44–2.66(4H, m), 3.22(2H, s), 4.70(1H, m), 4.98(1H, d, J=3.7 Hz), 6.35(1H, s), 7.11(2H, d, J=8.1 Hz), 7.22(2H, d,J=8.1 Hz), 11.38(1H, s)

MS m/z: 359(M$^+$)

2-[1-[2-Hydroxy-2-(2,4-dimethylphenyl)ethyl]-1,2,5,6-tetrahydropyrid-4-yl]-4H,6H-1,3,4-thiadiazin-5-one (Compound 25)

Yield: 49%

Appearance: white powder (recrystallization from methanol)

Melting Point: 178°–182° C. (dec.)

IR(KBr)cm$^{-1}$: 3191, 3109, 1675

NMR(DMSO-d$_6$) δ: 2.23(3H, s), 2.25(3H, s), 2.35–2.45(4H, m), 2.60–2.70 (2H, m), 3.20–3.30(2H, m), 3.36(2H, s), 4.90–4.95(2H, m), 6.91(1H, s), 6.97(1H, d, J=7.9 Hz), 7.32(1H, d, J=7.9 Hz), 11.39(1H, s)

MS m/z: 345 (M$^+$)

2-[1-[2-Hydroxy-2-(2-hydroxyphenyl)ethyl]-1,2,5,6-tetrahydropyrid-4-yl]-4H,6H-1,3,4-thiadiazin-5-one (Compound 26)

Yield: 51%

Appearance: light pink powder (recrystallization from chloroform)

Melting Point: 193°–195° C. (dec.)

IR(KBr)cm$^{-1}$: 3176, 3063, 3007, 1643

NMR(DMSO-d$_6$) δ: 2.42(2H, s), 2.51–2.60(2H, m), 2.68–2.70(2H, m), 3.29(2H, s), 3.42(2H, s), 5.00–5.10(2H, m), 6.42(1H, s), 6.75–6.85(2H, m), 7.05–7.10(1H, m), 7.31–7.33(1H, m), 10.10(1H, brs), 11.40(1H, s)

MS m/z: 333 (M$^+$)

2-[1-[2-Hydroxy-2-(3-hydroxyphenyl)ethyl]-1,2,5,6-tetrahydropyrid-4-yl]-4H,6H-1,3,4-thiadiazin-5-one (Compound 27)

Yield: 48%

Appearance: white powder (recrystallization from chloroform)

Melting Point: 148°–150° C. (dec.)

IR(KBr)cm$^{-1}$: 3179, 1662, 1602

NMR(DMSO-d$_6$) δ: 2.38(2H, s), 2.50–2.70(4H, m), 3.23(2H, s), 3.41(2H, s), 4.65 (1H, brs), 4.98 (1H, d, J=3.6 Hz), 6.40 (1H, s), 6.60(1H, d, J=8 Hz), 6.73–6.77(2H, m), 7.08 (1H, t, J=7.7 Hz), 9.25(1H, s), 11.38(1H, s)

MS m/z: 333(M$^+$)

2-[1-[2-Hydroxy-2-(2-nitrophenyl)ethyl]-1,2,5,6-tetrahydropyrid-4-yl]-4H,6H-1,3,4-thiadiazin-5-one (Compound 29)

Yield: 58%

Appearance: yellow powder (recrystallization from ethanol)

Melting Point: 207°–210° C. (dec.)

IR(KBr)cm$^{-1}$: 3217, 1674

NMR(DMSO-d$_6$) δ: 2.37(2H, s), 2.54–2.70(4H, m), 3.18(2H, s), 3.41(2H, s), 5.31(1H, brs), 5.54(1H, d, J=4.4 Hz), 6.38(1H, s), 7.50(1H, m), 7.72(1H, m), 7.85–7.90(2H, m),11.38(1H, s)

MS m/z: 362(M$^+$)

2-[1-[2-Hydroxy-2-(3-nitrophenyl)ethyl]-1,2,5,6-tetrahydropyrid-4-yl]-4H,6H-1,3,4-thiadiazin-5-one (Compound 30)

Yield: 66%

Appearance: yellow powder (recrystallization from chloroform-methanol)

Melting Point: 200°–202° C. (dec.)

IR(KBr)cm$^{-1}$: 3445, 3178, 3080, 1654

NMR(DMSO-d$_6$) δ: 2.37(2H, s), 2.50–2.80(4H, m), 3.15–3.30(2H, m), 3.41(2H, s), 4.90(1H, brs), 5.50(1H, d, J=4.4 Hz), 6.39(1H, s), 7.61(1H, t, J=8 Hz), 7.81(1H, d, J=8 Hz), 8.10(1H, d, J=8 Hz), 8.23(1H, s), 11.38(1H, s)

MS m/z: 362(M$^+$)

2-[1-[2-Hydroxy-2-[3,4-(methylenedioxy)phenyl]ethyl]-1,2,5,6-tetrahydropyrid-4-yl]-4H,6H-1,3,4-thiadiazin-5-one (Compound 32)

Yield: 58%

Appearance: light yellow powder (recrystallization from dichloromethanemethanol)

Melting Point: 180°–183° C. (dec.)

IR(KBr)cm$^{-1}$: 3243, 1662

NMR(CDCl$_3$-DMSO-d$_6$) δ: 2.50–2.70(5H, m), 2.80–2.90(1H, m), 3.15–3.45(2H+2H, m), 4.06(1H, s), 4.71(1H, t, J=6.8 Hz), 5.95 (2H, s), 6.45(1H, s), 6.77–6.83(2H, m), 6.90(1H, m), 10.37(1H, s)

MS m/z: 361 (M$^+$)

2-[1-[2-Hydroxy-2-(4-methoxyphenyl)ethyl]-1,2,5,6-tetrahydropyrid-4-yl]-4-methyl-4H,6H-1,3,4-thiadiazin-5-one (Compound 37)

Yield: 80%

Appearance: yellow powder (recrystallization from chloroform-methanol)

Melting Point: 135°–1 37° C. (dec.)

IR(KBr)cm$^{-1}$: 1660

NMR(CDCl$_3$) δ: 2.55–2.70(5H, m), 2.90–3.00(1H, m), 3.25–3.50(2H, m), 3.30(2H, m), 3.45(3H, s), 3.80(3H, s), 3.84(1H, d, J=4.3 Hz), 4.74(1H, t, J=6.9 Hz), 6.46(1H, s), 6.89(2H, d, J=8.6 Hz), 7.30(2H, d, J=8.6 Hz)

MS m/z: 361 (M$^+$)

2-[1-[2-(2-Chlorophenyl)-2-hydroxyethyl]-1,2,5,6-tetrahydropyrid-4-yl]-4-methyl-4H,6H-1,3,4-thiadiazin-5-one (Compound 38)

Yield: 72%

Appearance: yellow powder (recrystallization from dichloromethanediethyl ether)

Melting Point: 147°–150° C. (dec.)

IR(KBr)cm$^{-1}$: 3160, 1660

NMR(CDCl$_3$) δ: 2.40–3.00(6H, m), 3.31(2H, s), 3.46(2H, s), 3.23–3.60(2H, m), 3.92(1H, brs), 5.22(1H, d, J=4.2 Hz), 6.47(1H, s), 7.20–7.40(3H, m), 7.68(1H, d, J=7.2 Hz)

MS m/z: 365 (M$^+$)

2-[1-[2-Hydroxy-2-[2-(trifluoromethyl)phenyl]ethyl]-1,2,5,6-tetrahydropyrid-4-yl]-4H,6H-1,3,4-thiadiazin-5-one (Compound 33)

Yield: 60%

Appearance: light yellow powder (recrystallization from chloroformmethanol)

Melting Point: 205°–210° C. (dec.)

IR(KBr)cm$^{-1}$: 3191, 3088, 1661

NMR(DMSO-d$_6$) δ: 2.40–2.55(3H, m), 2.60–2.70(3H, m), 3.20–3.30(2H, m), 3.41(2H, s), 5.08(1H, brs), 5.41(1H, d, J=4 Hz), 6.42(1H, s), 7.46(1H, t, J=7.9 Hz), 7.65–7.75(2H, m), 7.81(1H, d, J=7.9 Hz), 11.38(1H, s)

MS m/z: 385 (M$^+$)

2-[1-[2-(4-Fluorophenyl)-2-hydroxyethyl]-1,2,5,6-tetrahydropyrid-4-yl]-4H,6H-1,3,4-thiadiazin-5-one (Compound 35)

Yield: 54%

Appearance: white powder (recrystallization from chloroform-methanol)

Melting Point: 185°–1 90° C. (dec.)

IR(KBr)cm$^{-1}$: 3171, 3089, 1665

NMR(DMSO-d$_6$) δ: 2.37(2H, s), 2.51–2.67(4H, m), 3.22(2H, s), 3.41(2H, s), (4.74(1H, brs), 5.14(1H, d, J=4 Hz), 6.39(1H, s), 7.10–7.15 2H, m), 7.40 –7.45(2H, m), 11.38(1H, s)

MS m/z: 335 (M$^+$)

2-[1-[2-(4-Aminophenyl)-2-hydroxyethyl]-1,2,5,6-tetrahydropyrid-4-yl]-4H,6H-1,3,4-thiadiazin-5-one (Compound 63)

Yield: 8.5%

Appearance: light yellow-white granules (recrystallization from ethanol)

Melting Point: 183.0°–183.5° C. (dec.)

IR(KBr)cm$^{-1}$: 3428, 3341, 3231, 3004, 1662, 1615

NMR(DMSO-d$_6$) δ: 2.37–2.63(6H, m), 3.21(2H, s), 3.40(2H, s), 4.55(1H, m), 4.67(1H, d, J=3.3 Hz), 4.88(2H, s), 6.40(1H, s), 6.50(2H, d, J=8.4 Hz), 6.98(2H, d, J=8.4 Hz), 11.36(1H, s)

MS m/z: 332 (M$^+$)

EXAMPLE 2

5-[1-[2-Hydroxy-2-(4-methoxyphenyl)ethyl]-1,2,5,6tetra-hydropyrid-4-yl]-3H,6H-1,3,4-thiadiazin-2-one (Compound 39)

1-[(4-Methoxyphenyl)carbonylmethyl]-4-(3H,6H-1,3,4-thiadiazin-2-one-5-yl)pyridinium bromide (760 mg, 1.8 mmol) was dissolved in methanol (8 ml) and gradually added with sodium borohydride (680 mg, 18 mmol) under ice-cooling and then stirred at room temperature overnight. The solvent was removed under reduced pressure. The residue obtained was added with dichloromethane, washed with water and dried over anhydrous magnesium sulfate. The residue obtained by evaporation was purified by column chromatography (dichloromethane-methanol=20:1) to obtain the titled compound (423 mg) as white crystals.

Yield: 67.7%

Melting Point: 191.5° C. (dec.) (recrystallization from ethanol)

IR(KBr)cm$^{-1}$: 3345, 3022, 1635

NMR(DMSO-d$_6$) δ: 2.35(2H, s), 2.44–2.64(4H, m), 3.23(2H, s), 3.73(3H, s), 3.92(2H, s), 4.69(1H, m), 4.93(1H, d, J=4 Hz), 6.41(1H, s), 6.87(2H, d, J=8.8 Hz), 7.26(2H, d, J=8.8 Hz), 11.36(1H, s)

MS m/z: 347(M$^+$)

In accordance with the procedure of Example 2, the following compounds were obtained from corresponding starting materials.

5-[1-(2-Hydroxy-2-phenylethyl)-1,2,5,6-tetrahydropyrid-4-yl]-3H,6H-1,3,4-thiadiazin-2-one (Compound 40)

Yield: 81.1%

Appearance: colorless plates (recrystallization from ethanol)

Melting Point: 177.5°–1 78° C. (dec.)

IR(KBr)cm$^{-1}$: 3168, 3076, 1642

NMR(DMSO-d$_6$) δ: 2.35(2H, s), 2.48–2.68(4H, m), 3.24(2H, d, J=2.9 Hz), 3.92(2H, s), 4.75(1H, m), 5.05(1H, d, J=4 Hz), 6.41(1H, s), 7.20–7.36(5H, m), 11.37(1H, s)

MS m/z: 317(M$^+$)

5-[1-[2-(2-Chlorophenyl)-2-hydroxyethyl]-1,2,5,6-tetrahydropyrid-4-yl]-3H,6H-1,3,4-thiadiazin-2-one (Compound 41)

Yield: 97.9%

Appearance: brown granules (recrystallization from ethanol)

Melting Point: 181.5°–1 82.0° C. (dec.)

IR(KBr)cm$^{-1}$: 3210, 3067, 1637

NMR(DMSO-d$_6$) δ: 2.37(2H, s), 2.53–2.69(4H, m), 3.27(2H, m), 3.93(2H, s), 5.13(1H, m), 5.32(1H, d, J=4.4 Hz), 6.42(1H, s), 7.24–7.62(4H, m), 11.37(1H, s)

MS m/z: 351 (M$^+$)

5-[1-[2-(4-Chlorophenyl)-2-hydroxyethyl]-1,2,5,6-tetrahydropyrid-4-yl]-3H,6H-1,3,4-thiadiazin-2-one (Compound 42)

Yield: 84.7%

Appearance: colorless micaceous crystals (recrystallization from ethanol)

Melting Point: 187°–188° C. (dec.)

IR(KBr)cm$^{-1}$: 3505, 3202. 3056, 1633

NMR(DMSO-d$_6$) δ: 2.42(2H, s), 2.47–2.68(4H, m), 3.22(2H, s), 3.92(2H, s), 4.75(1H, m), 4.77(1H, d, J=4.8 Hz), 6.40(1H, s), 7.34–7.39(4H, m), 11.36 (1H, s)

MS m/z: 351 (M$^+$)

5-[1-[2-Hydroxy-2-(4-methylphenyl)ethyl]-1,2,5,6-tetrahydropyrid-4-yl]-3H,6H-1,3,4-thiadiazin-2-one (Compound 43)

Yield: 81.3%

Appearance: white fine needles (recrystallization from ethanol)

Melting Point: 176°–176.5° C.(dec.)

IR(KBr)cm$^{-1}$: 3194, 3063, 1645

NMR(DMSO-d$_6$) δ: 2. 27(3H, s), 235(2H, s), 245–264(4H, m), 323(2H, s), 3.92(2H, s), 4.70(1H, m), 4.95(1H, d, J=4 Hz), 6.41(1H, s), 7.11(2H, d, J=8.1 Hz), 7.23(2H, d, J=8.1 Hz), 11.36(1H, s)

MS m/z: 331 (M$^+$)

5-[1-[2-Hydroxy-2-(3-hydroxyphenyl)ethyl]-1,2,5,6-tetrahydropyrid-4-yl]-3H,6H-1,3,4-thiadiazin-2-one (Compound 44)

Yield: 80.3%

Appearance: opaline prisms (recrystallization from ethanol)

Melting Point: 188.5°–1 89° C. (dec.)

IR(KBr)cm$^{-1}$: 3261, 3057, 1629

NMR(DMSO-d$_6$) δ: 2.36(2H, s), 2.45–2.66(4H, m), 3.23(2H, s), 3.92(2H, s), 4.66(1H, m), 4.95(1H, d, J=3.7 Hz), 6.41(1H, s), 6.59–7.10(4H, m), 9.22(1H, s), 11.36(1H, s)

MS m/z: 333(M$^+$)

5-[1-[2-(4-Fluorophenyl)-2-hydroxyethyl]-1,2,5,6-tetrahydropyrid-4-yl]-3H,6H-1,3,4-thiadiazin-2-one (Compound 46)

Yield: 80.5%

Appearance: colorless micaceous crystals (recrystallization from ethanol)

Melting Point: 184.5°–1 85.5° C. (dec.)

IR(KBr)cm$^{-1}$: 3507, 3198, 3058, 1635

NMR(DMSO-d$_6$) δ: 2.34(2H, s), 2.46–2.70(4H, m), 3.22(2H, s), 3.92(2H, s), 4.75(1H, m), 5.11(1H, d, J=3.7 Hz), 6.41(1H, s), 7.12(2H, dd, J=2.7 Hz, 5.9 Hz), 7.38(2H, dd, J=2.7 Hz, 5.9 Hz), 11.36(1H, s)

MS m/z: 335 (M$^+$)

5-[1-[2-Hydroxy-2-(2-naphthyl)ethyl]-1,2,5,6-tetrahydropyrid-4-yl]-3H,6H-1,3,4-thiadiazin-2-one (Compound 69)

Yield: 81.9%

Appearance: opaline powder (recrystallization from DMF)

Melting Point: 189.5°–191° C. (dec.)

IR(KBr)cm$^{-1}$: 335.5, 3199, 3054, 1654, 1636

NMR(DMSO-d$_6$) δ: 2.36(2H, s), 2.60–2.74(4H, m), 3.27(2H, s), 3.92(2H, s), 4.93(1H, m), 5.22(1H, d, J=4.0 Hz), 6.41(1H, s), 7.44–7.55(3H, m), 7.84–7.96(4H, m), 11.37(1H, s)

MS m/z: 367(M$^+$)

EXAMPLE 3

4,5-Dihydro-6-[1-[2-hydroxy-2-(4-methoxyphenyl) ethyl]-1,2,5,6-tetrahydropyrid-4-yl] pyridazin-3(2H)-one (Compound 49)

1-[(4-Methoxyphenyl)carbonylmethyl]-4-(4,5-dihydropyridazin-3(2H)-one -6-yl)pyridinium bromide (300 mg, 0.74 mmol) was dissolved in methanol (5 ml), gradually added with sodium borohydride (280 mg, 7.4 mmol) under ice cooling and then stirred at room temperature overnight. The :solvent was removed under reduced pressure. The residue obtained was added with dichloromethane, washed with water and dried over anhydrous magnesium sulfate. The solvent was removed to obtain the titled compound (145 mg) as colorless crystals.

Yield: 60%

Melting Point: 187°–189° C. (dec.) (recrystallization from ethanol)

IR(KBr)cm$^{-1}$: 3304, 1678, 1657

NMR(CDCl$_3$) δ: 2.47–2.93(6H, m), 3.21(1H, d, J=16 Hz), 3.44 (1H, d, J=16 Hz), 3.81(1H, s), 4.75(1H, m), 6.16(1H, brs), 6.89(2H, d, J=8.5 Hz), 7.31(2H, d, J=8.5 Hz), 8.41(1H, s)

MS m/z: 329(M$^+$)

In accordance with the procedure of Example 3, the following compounds were obtained from corresponding starting materials.

6-[1-[2-(2-Chlorophenyl)-2-hydroxyethyl]-1,2,5,6-tetrahydropyrid-4-yl]-4,5-dihydropyridazin-3 (2H)-one (Compound 50)

Yield: 90%

Appearance: colorless plates (recrystallization from ethanol)

Melting Point: 195°–202° C. (dec.)

NMR(CDCl$_3$) δ: 2.39–2.98(10H, m), 3.24(1H, d, J=18 Hz), 3.47(1H, d, J=18 Hz), 3.95(1H, br), 5.22(1H, dd, J=2 Hz, 10 Hz), 6.16(1H, brs), 7.18–7.34 (3H, m), 7.68(1H, d, J=7 Hz), 8.50(1H, s)

MS m/z: 333(M$^+$)

6-[1-[2-(4-Fluorophenyl)-2-hydroxyethyl]-1,2,5,6-tetrahydropyrid-4-yl]-4,5-dihydropyridazin-3 (2H)-one (Compound 51)

Yield: 78%

Appearance: colorless plates (recrystallization from ethanol)

Melting Point: 172°–180° C. (dec.)

IR(KBr)cm$^{-1}$: 3358, 3058, 1673

NMR(CDCl$_3$) δ: 2.47–2.96(10H, m), 3.21(1H, d, J=18 Hz), 3.44(1H, d, J=18 Hz), 3.95(1H, br), 4.77(1H, m), 6.15(1H,brs), 7.04(2H, m), 7.35(2H, m), 8.43(1H, s)

MS m/z: 317(M$^+$)

4,5-Dihydro-6-[1-[2-hydroxy-2-(2-methylphenyl) ethyl]-1,2,5,6-tetrahydropyrid-4-yl]pyridazin-3 (2H)-one (Compound 52)

Yield: 76%

Appearance: colorless plates (recrystallization from ethanol)

Melting Point: 181°–188° C. (dec.)

IR(KBr)cm$^{-1}$: 3226, 3134, 3071, 1685

NMR(CDCl$_3$) δ: 2.34(3H, s), 2.50–2.95(10H, m), 3.24(1H, d, J=18 Hz), 3.46 (1H, d, J=18 Hz), 3.84(1H, br), 5.06(1H, m), 6.16(1H, brs), 7.11–7.26 (3H, m), 7.57(1H, d, J=8 Hz), 8.51(1H, s)

MS m/z: 313(M$^+$)

4,5-Dihydro-6-[1-[2-hydroxy-2-(4-nitrophenyl) ethyl]-1,2,5,6-tetrahydropyrid-4-yl]pyridazin-3 (2H)-one (Compound 53)

Yield: 69%

Appearance: light yellow powder (recrystallization from ethanol)

Melting Point: 180°–183.5° C. (dec.)

IR(KBr)cm$^{-1}$: 3488, 3220, 3083, 1659

NMR(CDCl$_3$) δ: 2.47–2.79(9H, m), 2.92(1H, m), 3.23(1H, d, J=18 Hz), 3.45(1H, d, J=18 Hz), 4.13(1H, br), 7.57(2H, d, J=8.6 Hz), 8.22(2H, d, J=8.6 Hz), 8.49(1H, s)

MS m/z: 344 (M$^+$)

4,5-Dihydro-6-[1-[2-hydroxy-2-[2-(trifluoromethyl) phenyl]ethyl]-1,2,5,6-tetrahydropyrid-4-yl]pyridazin-3 (2H)-one (Compound 54)

Yield: 80%

Appearance: colorless plates (recrystallization from ethanol)

Melting Point: 219°–221° C.(dec.)

IR(KBr)cm$^{-1}$: 3239, 3146, 3066, 1691

NMR (DMSO-d$_6$) δ: 2.28–2.34(4H, m), 2.45(1H, m), 2.58–2.67(5H, m), 3.14–3.31 (2H, m), 5.09 (1H, m), 5.39(1H, d, J=4 Hz), 6.24(1H, s), 7.46(1H, m), 7.67(2H, m), 7.82 (1H, m), 10.71(1H, s)

MS m/z: 367 (M$^+$)

4,5-Dihydro-6-[1-(2-hydroxy-2-phenylethyl)-1,2,5,6-tetrahydropyrid-4-yl]pyridazin-3(2H)-one (Compound 55)

Yield: 78%

Appearance: light brown plates (recrystallization from ethanol)

Melting Point: 147°–155° C. (dec.)

IR(KBr)cm$^{-1}$: 3422, 3218, 3059, 1671

NMR(DMSO-d$_6$) δ: 2.09(2H, s), 2.28–2.32(4H, m), 2.51–2.67(4H, m), 3.20(2H, d, J=3 Hz), 4.74(1H, m), 5.03(1H, d, J=4 Hz), 6.22(1H, brs), 7.20–7.36(5H, m), 10.70(1H, s)

MS m/z: 299(M$^+$)

EXAMPLE 4

4,5-Dihydro-3-[1-[2-hydroxy-2-(4-methoxyphenyl) ethyl]-1,2,5,6-tetrahydropyrid-4-yl]-1,2,4-triazin-6(1H)-one(Compound 56 )

1-[(4-Methoxyphenyl)carbonylmethyl]-4-(4,5-dihydro-1,2,4-triazin-6(1H)-one-3-yl)pyridinium bromide (300 mg, 0.74 mmol) was dissolved in methanol (5 ml), gradually added with sodium borohydride (280 mg, 7.4 mmol) under ice cooling and stirred at room temperature overnight. The solvent was removed under reduced pressure. The residue obtained was added with dichloromethane, washed with water and dried over anhydrous magnesium sulfate. The solvent was removed to obtain the titled compound (165 mg) as colorless plates.

Yield: 68%

Melting Point: 190°–194° C. (dec.) (recrystallization from ethanol)

IR(KBr)cm$^{-1}$: 3299, 3200, 1655, 1610

NMR(DMSO-d$_6$) δ: 2.26(2H, br), 2.41–2.60(4H, m), 3.13(2H,br), 3.65(2H, br), 3.73(3H, s), 4.67(1H, m), 4.90(1H, d,J=4 Hz), 6.20(1H, brs), 6.77(1H, s), 6.86(2H, d, J=8.5 Hz), 7.27(2H, d, J=8.5 Hz), 10.23(1H, s)

MS m/z: 330 (M$^+$)

In accordance with the procedure of Example 4, the following compounds were obtained from corresponding starting materials.

3-[1-[2-(4-Chlorophenyl)-2-hydroxyethyl]-1,2,5,6-tetrahydropyrid-4-yl]-4,5-dihydro-1,2,4-triazin-6(1H)-one (Compound 57)

Yield: 75%

Appearance: colorless plates (recrystallization from ethanol)

Melting Point: 193°–198° C. (dec.)

IR(KBr)cm$^{-1}$: 3310, 3185, 1655, 1607

NMR(DMSO-d$_6$) δ: 2.25(2H, br), 2.44–2.62(4H, m), 3.13(2H,d, J=3 Hz), 3.65(2H, s), 4.74(1H, m), 5.16(1H, d, J=4 Hz), 6.20(1H, brs), 6.77(1H, s), 7.33–7.39(4H, s), 10.24(1H, s)

MS m/z: 334 (M$^+$)

4,5-Dihydro-3-[1-[2-hydroxy-2-(4-methylphenyl)ethyl]-1,2,5,6-tetrahydropyrid-4-yl]-1,2,4-triazin-6(1H)-one (Compound 58)

Yield: 87%

Appearance: colorless plates (recrystallization from methyl cellosolve)

Melting Point: 200°–205° C. (dec.)

IR(KBr)cm$^{-1}$: 3301, 3186, 1656, 1608

NMR(DMSO-d$_6$) δ: 2.27(3H+2H, brs), 2.42–2.61(4H, m), 3.13(2H, d, J=2.6 Hz), 3.65(2H, s), 4.69(1H, m), 4.92(1H, m), 6.20(1H, brs), 6.76(1H, s), 7.10(2H, d, J=8 Hz), 7.22(2H,d, J=8 Hz), 10.23(1H, s)

MS m/z: 314(M$^+$)

3-[1-[2-(4-Fluorophenyl)-2-hydroxyethyl]-1,2,5,6-tetrahydropyrid-4-yl]-4,5-dihydro-1,2,4-triazin-6(1H)-one (Compound 59)

Yield: 62%

Appearance: colorless plates (recrystallization from ethanol)

Melting Point: 203°–206° C. (dec.)

IR(KBr)cm$^{-1}$: 3307, 3197, 3031, 1656, 1604

NMR(DMSO-d$_6$) δ: 2.25(2H, brs), 2.43–2.62(4H, m), 3.13(2H,d, J=3 Hz), 3.66(2H, d, J=1.5 Hz), 4.74(1H, m), 5.10(1H, m), 6.20(1H, brs), 6.77(1H, s), 7.09–7.14(2H, m), 7.35–7.39(2H, m), 10.24(1H, s)

MS m/z: 318(M$^+$)

4,5-Dihydro-3-[1-[2-hydroxy-2-(4-nitrophenyl)ethyl]-1,2,5,6-tetrahydropyrid-4-yl]-1,2,4-triazin-6(1H)-one (Compound 60)

Yield: 70%

Appearance: light yellow powder (recrystallization from methyl cellosolve)

Melting Point: 193°–197° C. (dec.)

IR(KBr)cm$^{-1}$: 3321, 3198, 1654

NMR(DMSO-d$_6$) δ: 2.25(2H, brs), 2.50–2.66(4H, m), 3.14(2H,brs), 3.66(2H, s), 4.89(1H, m), 5.46(1H, d, J=4 Hz), 6.20(1H, s), 6.78(1H, s), 7.64(2H, d, J=8.5 Hz), 8.19(2H, d, J=8.5 Hz), 10.25(1H, s)

MS m/z: 345(M$^+$)

4,5-Dihydro-3-[1-[2-hydroxy-2-[2-(trifluoromethyl)phenyl]ethyl]-1,2,5,6-tetrahydropyrid-4-yl]-1,2,4-triazin-6(1H)-one (Compound 61)

Yield: 77%

Appearance: colorless plates (recrystallization from ethanol)

Melting Point: 210°–214° C. (dec.)

IR(KBr)cm$^{-1}$: 3338, 3259, 1663, 1608

NMR(DMSO-d$_6$) δ: 2.28(2H, brs), 2.43(1H, m), 2.51°–2.62(3H, m), 3.09–3.21 (2H, m), 3.66(2H, s), 5.08(1H, m), 5.39 (1H, d, J=4 Hz), 6.21(1H, s), 6.78(1H, s), 7.46(1H, m), 7.64–7.70(2H, m), 7.81(1H, m), 10.25(1H, s)

MS m/z: 368 (M$^+$)

4,5-Dihydro-3-[1-(2-hydroxy-2-phenylethyl)-1,2,5,6-tetrahydropyrid-4-yl]-1,2,4-triazin-6(1H)-one (Compound 62)

Yield: 79%

Appearance: colorless plates (recrystallization from ethanol)

Melting Point: 204°–208° C. (dec.)

IR(KBr)cm$^{-1}$: 3294, 3169, 3031, 1655, 1609

NMR(DMSO-d$_6$) δ: 2.26(2H, brs), 2.44–2.62(4H, m), 3.14(2H, d, J=3 Hz), 3.66(2H, s), 4.73(1H, m), 5.04(1H, d, J=4 Hz), 6.21(1H, s), 6.78(1H, s), 7.20–7.36(5H, m), 10.25(1H, s)

MS m/z: 300 (M$^+$)

3-[1-[2-(4-Cyanophenyl)-2-hydroxyethyl]-1,2,5,6-tetrahydropyrid-4-yl]-4,5-dihydro-1,2,4-triazin-6(1H)-one (Compound 64)

Yield: 91%

Appearance: yellow crystals (recrystallization from ethanol)

Melting Point: 206°–209° C. (dec.)

IR(KBr)cm$^{-1}$: 3336, 3253, 2226, 1663, 1607

NMR(DMSO-d$_6$) δ:2.23(2H, brs), 2.44–2.74(4H, m), 3.12(2H,brs), 3.64(2H, s), 4.82(1H, m), 3.53(1H, d, J=4.3 Hz), 6.18(1H, brs), 6.76(1H, s), 7.54 (2H, d, J=8.6 Hz), 7.77 (2H, d, J=8.6 Hz), 10.23(1H, s)

MS m/z: 325(M$^+$)

3-[1-[2-(4-Aminophenyl)-2-hydroxyethyl]-1,2,5,6-tetrahydropyrid-4-yl]-4,5-dihydro-1,2,4-triazin-6(1H)-one (Compound 65)

Yield: 67%

Appearance: opaline crystals (recrystallization from ethanol)

Melting Point: 213°–216° C. (dec.)

IR(KBr)cm$^{-1}$: 3364, 3039, 1643. 1615

NMR(DMSO-d$_6$) δ: 2.26(2H, brs), 2.37–2.79(4H, m), 3.12(2H,brs), 3.66(2H, s), 4.56(1H, m), 4.64(1H, d, J=3.6 Hz), 4.88(2H, s), 6.20(1H, brs), 6.49(2H, d, J=8.2 Hz), 6.76 (1H, s), 6.98(2H, d, J=8.2 Hz), 10.23(1H, s)

MS m/z: 315(M$^+$)

4,5-Dihydro-3-[1-[2-hydroxy-2-(2-nitrophenyl)ethyl]-1,2,5,6-tetrahydropyrid-4-yl]-1,2,4-triazin-6(1H)-one (Compound 66)

Yield: 75%

Appearance: light yellow-brown crystals (recrystallization from ethanol)

Melting Point: 195°–197° C. (dec.)

IR(KBr)cm$^{-1}$: 3333, 3258, 3102, 1663, 1611

NMR(DMSO-d$_6$) δ: 2.24(2H, brs), 2.45–2.76(4H, m), 3.10(2H,brs), 3.66(2H, s), 5.28(1H, m), 5.52(1H, d, J=4.3 Hz), 6.18(1H, brs), 6.76(1H, s), 7.46–7.93(4H, m), 10.23(1H, s)

MS m/z: 345(M$^+$)

4,5-Dihydro-3-[1-[2-hydroxy-2-(3-nitrophenyl)ethyl]-1,2,5,6-tetrahydropyrid-4-yl]-1,2,4-triazin-6(1H)-one (Compound 67)

Yield: 85%

Appearance: light brown crystals (recrystallization from ethanol)

Melting Point: 185°–1 87.5° C. (dec.)

IR(KBr)cm$^{-1}$: 3329, 3070, 1655, 1602

NMR(DMSO-d$_6$) δ: 2.26(2H, brs), 2.45–3.10(4H, m), 3.16(2H,brs), 3.66(2H,s), 4.91 (1H, m), 5.48(1H, d, J=4.0 Hz), 6.20 (1H, brs), 6.77 (1H, s), 7.58–8.23(4H, m), 10.24(1H,s)

MS m/z: 345(M$^+$)

4,5-Dihydro-3-[1-[2-hydroxy-2-[3,4-(methylenedioxy)phenyl]ethyl]-1,2,5,6-tetrahydropyrid-4-yl]-1,2,4-triazin-6(1H)-one (Compound 68)

Yield: 92%

Appearance: colorless minute scales (recrystallization from ethanol)

Melting Point: 198.5°–201.5° C. (dec.)

IR(KBr)cm$^{-1}$: 3317, 3223, 3052, 1653, 1612

NMR(DMSO-d$_6$) δ: 2.26(2H, brs), 2.39–2.62(4H, m), 3.13(2H,d, J=2.6 Hz), 3.66(2H, d, J=1.0 Hz), 4.65(1H, m), 4.96(1H,d, J=4.0 Hz), 5.96(2H, s), 6.20(1H, brs), 6.76(1H, s), 6.81(2H, s), 6.89(1H, s), 10.23(1H, s)

MS m/z: 344 (M$^+$)

4,5-Dihydro-3-[1-[2-hydroxy-2-(4-hydroxyphenyl)ethyl]-1,2,5,6-tetrahydropyrid-4-yl]-1,2,4-triazin-6(1H)-one (Compound 72)

Yield: 29%

Appearance: white powder (recrystallization from ethanol)

Melting Point: 211°–2! 3° C. (dec.)

IR(KBr)cm$^{-1}$: 3309, 3230, 1663, 1617

NMR(DMSO-d$_6$) δ: 2.26(2H, brs), 2.37–2.59(4H, m), 3.12(2H,d, J=2.0 Hz), 3.66(2H, s), 4.62(1H, m), 4.80(1H, d, J=3.6 Hz), 6.20(1H, brs), 6.68(2H, d, J=8.6 Hz), 6.77(1H, s), 7.12(2H, d, J=8.6 Hz), 9.20(1H, s), 10.24(1H, MS m/z: 316(M$^+$)

EXAMPLE 5

2-[1-[2-(2-Chlorophenyl)-2-hydroxyethyl]-1,2,5,6-tetrahydropyrid-4-y 1]-6-methyl-4H,6H-13,4-thiadiazin-5-one (Compound 10)

6-Methyl-2-(4-pyridyl)-4H,6H-1,3,4-thiadiazin-5-one (415 mg, 2 mmol) and 2'-chlorophenacyl bromide (654 mg, 2.8 mmol) were dissolved in absolute ethanol (6 ml) and stirred at room temperature for one day. The solvent was removed under reduced pressure to obtain 1-[(2-chlorophenyl)carbonylmethyl]-4-(6-methyl-4H,6H-1,3,4-thiadiazin-5-one-2-yl)pyridinium bromide as yellow brown gum. The salt was dissolved in methanol (7 ml), gradually added with sodium borohydride (756 mg, 20 mmol) under ice cooling and stirred at room temperature overnight. The solvent was removed under reduced pressure. The residue obtained was separated by column chromatography (dichloromethane-methanol=40:1) and purified to obtain the titled compound (621 mg) as opaline plates.

Yield: 84.7%

Melting Point: 184°–185° C. (dec.) (recrystallization from ethanol)

IR(KBr)cm$^{-1}$: 3198, 3099, 1671

NMR(DMSO-d$_6$) δ: 1.27(3H, d, J=7 Hz), 2.41(2H, s), 2.52°–2.71(4H, m), 3.26(2H, m), 3.61(1H, q, J=6.7 Hz), 5.12(1H, m), 5.32(1H, d, J=4.4 Hz), 6.40 (1H, s), 7.24–7.62(4H, m), 11.38(1H, s)

MS m/z: 365(M$^+$)

In accordance with the procedure of Example 5, the following compounds were obtained from corresponding starting materials.

2-[1-[2-Hydroxy-2-(4-hydroxyphenyl)ethyl]-1,2,5,6-tetrahydropyrid-4-yl]-4H,6H-1,3,4-thiadiazin-5-one (Compound 28)

Yield: 64%

Appearance: light purple powder (recrystallization from ethanol)

Melting Point: 206°–207° C. (dec.)

IR(KBr)cm$^{-1}$: 3398, 3008, 1676

NMR(DMSO-d$_6$) δ: 2.35–2.65(6H, m), 3.22(2H, s), 3.40(2H, s), 4.63(1H, brs), 4.83(1H, s), 6.40(1H, s), 6.68(2H, d,J=8.4 Hz), 7.12(2H, d, J=8.4 Hz), 9.25(1H, brs), 11.36(1H,s)

MS m/z: 333 (M$^+$)

2-[1-[2-Hydroxy-2-(4-nitrophenyl)ethyl]-1,2,5,6-tetrahydropyrid-4-yl]-4H,6H-1,3,4-thiadiazin-5-one (Compound 31)

Yield: 62%

Appearance: yellow powder (recrystallization from dichloromethane)

Melting Point: 196°–197° C. (dec.)

IR(KBr)cm$^{-1}$: 3443, 3180, 3080, 1659

NMR(DMSO-d$_6$) δ: 2.37(2H, s), 2.51–2.70(4H, m), 3.23(2H, s), 3.40(2H, s), 4.89(1H, brs), 5.48(1H, d, J=4 Hz), 6.39(1H, s), 7.64(2H, d, J=8.8 Hz), 8.19(2H, d, J=8.5 Hz), 11.38(1H, s)

MS m/z: 362 (M$^+$)

2-[1-[2-Hydroxy-2-[3-(trifluoromethyl)phenyl]ethyl]-1,2,5,6-tetrahydropyrid-4-yl]-4H,6H-1,3,4-thiadiazin-5-one (Compound 34)

Yield: 57%

Appearance: white powder (recrystallization from chloroform-methanol)

Melting Point: 205°–207° C. (dec.)

IR(KBr)cm$^{-1}$: 3462, 3178, 3081, 1660

NMR(DMSO-d$_6$) δ: 2.38(2H, s), 2.51–2.69(4H, m), 3.25(2H, s), 3.41(2H, s), 4.80(1H, brs), 5.34(1H, d, J=4.4 Hz), 6.39(1H, s), 7.53(1H, t, J=7 Hz), 7.58(1H, d, J=7 Hz), 7.65(1H, d, J=7 Hz), 7.70(1H, s), 11.37(1H, s)

MS m/z: 385 (M$^+$)

2-[1-[2-Hydroxy-2-(4-isopropylphenyl)ethyl]-1,2,5,6-tetrahydropyrid-4-yl]-4H,6H-1,3,4-thiadiazin-5-one (Compound 36)

Yield: 61%

Appearance: white powder (recrystallization from chloroform-methanol)

Melting Point: 196°–206° C. (dec.)

IR(KBr)cm$^{-1}$: 3453, 3180, 3082, 1660

NMR(CDCl$_3$-DMSO-d$_6$) δ: 1.24(6H, d, J=1.8 Hz), 2.44(1H, brs), 2.50–2.70(4H, m), 2.85–2.95(2H, m), 3.20–3.50(4H, brs), 3.95(1H, brs), 4.77(1H, t, J=6.8 Hz), 6.48(1H, brs), 7.20(2H, d, J=8.3 Hz), 7.30(2H, d, J=8.3 Hz), 10.05(1H, s)

MS m/z: 359(M$^+$)

5-[1-[2-Hydroxy-2-(4-nitrophenyl)ethyl]-1,2,5,6-tetrahydropyrid-4-yl]-3H,6H-1,3,4-thiadiazin-2-one (Compound 45)

Yield: 59.4%

Appearance: light brown micaceous crystals (recrystallization from ethanol)

Melting Point: 186.5°–187° C. (dec.)

IR(KBr)cm$^{-1}$: 3194. 3074. 1639

NMR(DMSO-d$_6$) δ: 2.34(2H, s), 2.54–2.71(4H, m), 3.24(2H, s), 3.92(2H, s), 4.92(1H, m), 5.46(1H, d, J=4.4 Hz), 6.40 (1H, s), 7.64(2H, d, J=8.4 Hz), 8.14(2H, d, J=8.4 Hz), 11.37(1H,s)

MS m/z: 362(M$^+$)

5-[1-[2-(4-Cyanophenyl)-2-hydroxyethyl]-1,2,5,6-tetrahydropyrid-4-yl]- 3H,6H-1,3,4-thiadiazin-2-one (Compound 47)

Yield: 82.7%

Appearance: light brown micaceous crystals (recrystallization from ethanol)

Melting Point: 189.5°–191.5° C. (dec.)

IR(KBr)cm$^{-1}$: 3212, 3083, 2225,1637

NMR (DMSO-d$_6$) δ: 2.34 (2H, s), 2.52–2.70(4H, m), 3.23(2H, m), 3.92(2H, m), 4.86(1H, m), 5.38(1H, d, J=4.4 Hz), 6.40 (1H, s), 7.56(2H, d, J=8.4 Hz), 7.77(2H, d, J=8.4 Hz), 11. 37(1H,s)

MS m/z: 342(M$^+$)

5-[1-[2-Hydroxy-2-[3-(trifluoromethyl)phenyl]ethyl]-1,2,5,6-tetrahydropyrid-4-yl]-3H,6H-1,3,4-thiadiazin-2-one (Compound 48)

Yield: 84.2%

Appearance: white crystals (recrystallization from ethanol)

Melting Point: 174.5°–175.5° C. (dec.)

IR(KBr)cm$^{-1}$: 3185, 3077, 1638

NMR(DMSO-d$_6$) δ: 2.35(2H, s), 2.52–2.70(4H, m), 3.24(2H, m), 3.92(2H, m), 4.87(1H, m), 5.33(1H, d, J=4 Hz), 6.41(1H, s), 7.52–7.71(4H, m), 11.36(1H, s)

MS m/z: 385 (M$^+$)

EXAMPLE 6

2-[1-[2-Methoxy-2-(4-methoxyphenyl)ethyl]-1,2,5,6-tetrahydropyrid-4-yl]-4H,6H-1,3,4-thiadiazin-5-one (Compound 70)

2-[1-[2-Hydroxy-2-(4-methoxyphenyl)ethyl]-1,2,5,6-tetrahydropyrid-4-yl]-4H,6H-1,3,4-thiadiazin-5-one (150 mg, 0.43 mmol) was dissolved in methanol (5 ml), added with concentrated sulfuric acid (0.8 ml, 15 mmol) and refluxed with heating for four hours. The solution was poured into ice water and neutralized with 2N aqueous sodium hydroxide.

The precipitated colorless crystals are filtered out and recrystallized from 60% aqueous ethanol solution to obtain the compound (110 mg) as light yellow fine needles.

Yield: 70%

Melting Point: 154°–155° C. (dec.)

IR(KBr)cm$^{-1}$: 3162, 3073, 1669, 1609

NMR(CDCl$_3$) δ: 2.50–2.90(6H, m), 3.20(3H, s), 3.31(4H, brs), 3.81(3H, s), 4.36(1H, m), 6.46(1H, brs), 6.90(2H, d, J=8.5 Hz), 7.25(2H, d, J=8.5 Hz), 8.75(1H, brs)

MS m/z: 359(M$^+$)

In accordance with the procedure of Example 6, the following compound was obtained from corresponding starting material.

3-[1-[2-(4-Chlorophenyl)-2-methoxyethyl]-1,2,5,6-tetrahydropyrid-4-yl]-4,5-dihydro-1,2,4-triazin-6 (1H)-one (Compound 73)

Yield: 15%

Appearance: yellow powder

Melting Point: 168.5° C.<(dec.)

NMR(CD$_3$OD) δ: 2.42(2H, brs), 2.54–2.81(4H, m), 3.26–3.35(4H, m), 3.84(3H, s), 4.78–4.82(1H, m), 6.20(1H, s), 7.35(4H, s)

MS m/z: 348(M$^+$)

EXAMPLE 7

2-[1-[2-Isopropoxy-2-(4-methoxyphenyl)ethyl]-1,2,5,6-tetrahydropyrid-4-yl]-4H,6H-1,3,4-thiadiazin-5-one (Compound 71)

2-[1-[2-Hydroxy-2-(4-methoxyphenyl)ethyl]-1,2,5,6-tetrahydropyrid-4-yl]-4H,6H-1,3,4-thiadiazin-5-one (300 mg, 0.86 mmol) was suspended in mixed solution of isopropanol(15 ml) and benzene (25 ml), added with p-toluenesulfonic acid monohydrate (4.5 g, 0.02 mol) and refluxed for 5 hours while being dehydrated by a Dean-Stark's dehydrator. After allowing to cool to room temperature, the reaction mixture was added dropwise to 1N aqueous sodium hydroxide (30 ml). The benzen layer was separated and the water layer was further extracted three times with benzen. The benzen layer was combined with the above-mentioned benzen layer and dried over anhydrous magnesium sulfate. Benzene was removed under reduced pressure and the residue was crystallized from a little amount of ether. The solid obtained was further crystallized from ether to obtain the titled compound (145 mg) as white power.

Yield: 43%
Melting Point: 126°–127.5° C. (dec.)
IR(KBr)cm$^{-1}$: 3206, 3099, 1666
NMR(DMSO-d$_6$) δ: 0.98(3H, d, J=5.9 Hz), 1.09(3H, d, J=5.9 Hz), 2.35–2.74 (7H, m), 3.13–3.30(2H, m), 3.40(2H, s), 3.74(3H, s), 4.54–4.58(1H, m), 6.38(1H, s), 6.88(2H, d, J=8.6 Hz), 7.24(2H, d, J=8.6 Hz), 11.36(1H, s)
MS m/z: 389(M$^+$)

EXAMPLE 8

Hydrochloride of
2-[1-[2-(4-chlorophenyl)-2-hydroxyethyl]-1,2,5,6-tetrahydropyrid-4-yl]-4H,6H-1,3,4-thiadiazin-5-one (Compound 13)

2-[1-[2-(4-Chlorophenyl)-2-hydroxyethyl]-1,2,5,6-tetrahydropyrid-4-yl]-4H,6H-1,3,4-thiadiazin-5-one (2.5 g, 7.1 mmol) was added to 4N hydrochloric acid/dioxane solution and stirred at room temperature for 15 minutes. The resulting precipitate was collected by filtration, washed with absolute acetone and dried in vacuum to obtain the titled hydrochloride (2.7 g) as yellow powder.

Yield: quantitative
Melting Point: 149°–152° C. (dec.)
IR(KBr)cm$^{-1}$: 3259, 3204, 3106, 1686

In accordance with the procedure of Example 8, the following compounds were obtained from corresponding starting materials.

Hydrochloride of
2-[1-[2-hydroxy-2-(3-methylphenyl)ethyl]-1,2,5,6-tetrahydropyrid-4-yl]-4H,6H-1,3,4-thiadiazin-5-one
(Compound 20)

Yield: 56%
Appearance: light yellow powder
Melting Point: 193°–196° C. (dec.)
IR(KBr)cm$^{-1}$: 3237, 1699, 1667

Hydrochloride of
2-[1-[2-hydroxy-2-(4-methylphenyl)ethyl]-1,2,5,6-tetrahydropyrid-4-yl]-4H,6H-1,3,4-thiadiazin-5-one
(Compound 21)

Yield: quantitative
Appearance: yellow powder
Melting Point: 215°–220° C. (dec.)
IR(KBr)cm$^{-1}$: 3284, 3197, 3100, 1674

Hydrochloride of
2-[1-[2-hydroxy-2-(2,4-dimethylphenyl)ethyl]-1,2,5,6-tetrahydropyrid-4-yl]-4H,6H-1,3,4-thiadiazin-5-one (Compound 25)

Yield: 91%
Appearance: light pink powder
Melting Point: 207°–209° C. (dec.)
IR(KBr)cm$^{-1}$: 3226, 1676

Hydrochloride of
2-[1-[2-hydroxy-2-(3-nitrophenyl)ethyl]-1,2,5,6-tetrahydropyrid-4-yl]-4H,6H-1,3,4-thiadiazin-5-one
(Compound 30)

Yield: quantitative
Appearance: white powder
Melting Point: 157°–162° C.(dec.)
IR(KBr)cm$^{-1}$: 3205, 3096, 1681

Hydrochloride of
2-[1-[2-(4-fluorophenyl)-2-hydroxyethyl]-1,2,5,6-tetrahydropyrid-4-yl]-4H,6H-1,3,4-thiadiazin-5-one (Compound 35)

Yield: quantitative
Appearance: white powder
Melting Point: 200°–205° C. (dec.)
IR(KBr)cm$^{-1}$: 3259. 1686, 1665

Hydrochloride of
4,5-dihydro-3-[1-[2-hydroxy-2-(4-nitrophenyl)ethyl]-1,2,5,6-tetrahydropyrid-4-yl]-1,2,4-triazin-6(1H)-one (Compound 60)

Yield: 90%
Appearance: white fine needles (recrystallization from ethanol)
Melting Point: 200°–203° C. (dec.)
IR(KBr)cm$^{-1}$: 3274. 1654

EXAMPLE 9

Oxalate of
2-[1-[2-hydroxy-2-(4-methylphenyl)ethyl]-1,2,5,6-tetrahydropyrid-4-yl]-4H,6H-1,3,4-thiadiazin-5-one (Compound 21)

2-[1-[2-Hydroxy-2-(4-methylphenyl)ethyl]-1,2,5,6-tetrahydropyrid-4-yl]-4H,6H-1,3,4-thiadiazin-5-one (100 mg, 0.3mmol) was suspended in ethanol (4 ml) and was added with oxalic acid (39 mg, 0.3 mmol). Then, the suspension was stirred at room temperature for two hours and evaporated under reduced pressure. The residue was added with a little amount of methanol and then ether to precipitate solid. The solid was collected by filtration and dried in vacuum to obtain the titled oxalate (123 mg) as white powder.

Yield: 97%
Melting Point: 115°–1 20° C. (dec.)
IR(KBr)cm$^{-1}$: 3226, 3008, 1665

CAPABILITY OF EXPLOITATION IN INDUSTRY

The compounds of the present invention can selectively increase contraction force of cardiac muscles without increasing heart rate and therefore is effective as cardiotonic agent for cure and prevention of acute and chronic heart failure.

We claim:

1. A heterocyclic compound represented by the formula (I) or a pharmaceutically-acceptable acid addition salt thereof:

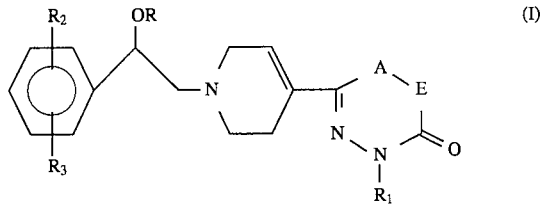

wherein R and $R_1$ represent hydrogen or lower alkyl; $R_2$ and $R_3$ are independently the same or different and each represents hydrogen, lower alkyl, lower alkoxy, trifluoromethyl, halogen, nitro, amino, cyano or hydroxyl, or $R_2$ and $R_3$ are joined to form methylenedioxy or a group of the formula:

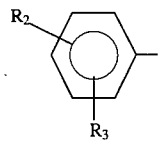

to form a naphthalene ring; and A–E represents:

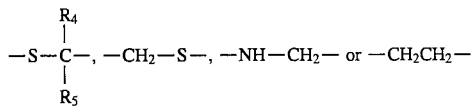

wherein $R_4$ and $R_5$ represent hydrogen or lower alkyl; or racemates or optical isomers thereof.

2. The compound of claim 1, wherein $R_1$ represents hydrogen.

3. The compound of claim 2, wherein A–E represents —S—$CH_2$—, —$CH_2$—S—, —NH—$CH_2$— or —$CH_2CH_2$—.

4. The compound of claim 1, wherein $R_1$ is hydrogen and A–E represents —S—$CH_2$—.

5. The compound of claim 1, wherein $R_1$ represents hydrogen; $R_2$ and $R_3$ are independently the same or different and each represents hydrogen, lower alkyl, lower alkoxy, trifluoromethyl, halogen, nitro, cyano or hydroxyl, or $R_2$ and $R_3$ are joined to form methylenedioxy; and A–E represents —S—$CH_2$—.

6. The compound of claim 1, wherein $R_1$ represents hydrogen and A–E represents —$CH_2$—S—.

7. The compound of claim 1, wherein $R_1$ is hydrogen; $R_2$ and $R_3$ are independently the same or different and each represents hydrogen, lower alkyl, trifluoromethyl, halogen, nitro, cyano or hydroxyl; and A–E represents —$CH_2$—S—.

8. The compound of claim 1, wherein $R_1$ represents hydrogen and A–E represents —NH—$CH_2$—.

9. The compound of claim 1, wherein $R_1$ is hydrogen; $R_2$ and $R_3$ are independently the same or different and each represents hydrogen, halogen, cyano or nitro; and A–E represents —NH—$CH_2$—.

10. The compound of claim 1, wherein $R_1$ represents hydrogen and A–E represents —$CH_2CH_2$—.

11. The compound of claim 1, wherein $R_1$ represents hydrogen; $R_2$ and $R_3$ are independently the same or different and each represents hydrogen, halogen, cyano or nitro; and A–E represents —$CH_2CH_2$—.

12. The compound of claim 1, which is 3-(1-(2-(4-chlorophenyl)-2-hydroxyethyl)-1,2,5,6-tetrahydropyrid-4-yl)-4,5-dihydro-1,2,4-triazin-6(1H)-one or 4,5-dihydro-3-(1-(2-hydroxy-2-(4-nitrophenyl)ethyl)-1,2,5,6-tetrahydropyrid-4-yl)-1,2,4-triazin-6(1H)-one.

13. The compound of any one of claims 1–12, which is a racemate.

14. The compound of any one of claims 1–12, which is either one or the other optical isomer.

15. A pharmaceutical composition, comprising one or more compounds of claim 1, as a cardiotonic active component, and a pharmaceutically-acceptable diluent or carrier.

* * * * *